US006416977B1

(12) United States Patent
Becher

(10) Patent No.: US 6,416,977 B1
(45) Date of Patent: Jul. 9, 2002

(54) FLEA CHITINASE NUCLEIC ACID MOLECULES AND USES THEREOF

(75) Inventor: Anna M. Becher, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/545,814

(22) Filed: Apr. 7, 2000

Related U.S. Application Data
(60) Provisional application No. 60/128,833, filed on Apr. 9, 1999.

(51) Int. Cl.[7] .................. C07H 21/04; C12P 21/00; C12N 1/21; C12N 7/00; C07K 14/20
(52) U.S. Cl. ............... 435/69.1; 435/252.3; 435/320.1; 536/23.6; 530/350
(58) Field of Search .................. 536/23.2; 435/69.1, 435/252.3, 320.1; 530/350

(56) References Cited

U.S. PATENT DOCUMENTS 5,573,915 A * 11/1996 Barry et al.

OTHER PUBLICATIONS

Ngo et al., in The Protein Folding Problem and Tertiary Structure Prediction, 1994, Merz, et al., (ed.), Birkhauser, Boston, MA, pp. 433 and 492–495.*
Voet et al., in Biochemistry. John Wiley & Sons. 1990, vol. 1, pp. 126–128, and p. 230.*
Sambrook et al., in Molecular Cloning A Laboratory Manual, 1989 second edition, Cold Spring Harbor Laboratory Press, Cold Spring Harbor, NY, p. 17.5–17.25.*
Kim et al, EMBL, Jan. 1997, Accession number AAB47538.1.*
Cohen–Kupiec, et al., *Current Opinion in Biotechnology*, vol. 9, 1998, pp. 270–277.
de la Vega, et al., *Insect Molecular Biology*, vol. 7, No. 3, 1998, pp. 233–239.
Heath, et al., *Parasite Immunology*, vol. 16, 1994, pp. 187–191.
Sim, et al., *Insect Biochemistry and Molecular Biology*, vol. 28, 1998, pp. 163–171.
Koga et al., *Insect Biochem. Molec. Biol.*, vol. 27, No. 8/9, 1997, pp. 757–767.
Kramer, et al., *Insect Biochem. Molec. Biol.*, vol. 2 No. 11, 1997, pp. 887–900.
Nielsen, et al., *Plant Physiol.*, vol. 113, 1997, pp. 83–91.
Niño–Vega, et al., *Yeast,* vol. 14, 1998, pp. 181–187.
Raghavan, et al., *Infection and Immunity,* vol. 62, No. 5, May 1994, pp. 1901–1908.
Shahabuddin, M., *Parasitology Today,* vol. 11, No. 2, 1995, pp. 46–47.
Shahabuddin, et al., *Parasitology Today,* vol. 9, No.7, 1993, pp. 252–255.
Spindler–Barth, et al., *Pestic Sci.,* vol. 52, 1998, pp. 47–52.
Willadsen, et al., *Parasitology Today,* vol. 9, No. 4, 1993, pp. 132–135.

* cited by examiner

Primary Examiner—Christina Y. Chan
Assistant Examiner—Phuong Huynh
(74) Attorney, Agent, or Firm—Heska Corporation

(57) ABSTRACT

The present invention relates to flea chitinase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from flea infestation.

12 Claims, No Drawings

SEQUENCE LISTING

<160> NUMBER OF SEQ ID NOS: 40

<210> SEQ ID NO 1
<211> LENGTH: 2610
<212> TYPE: DNA
<213> ORGANISM: Ctenocephalides felis
<220> FEATURE:
<221> NAME/KEY: CDS
<222> LOCATION: (1)..(1749)

<400> SEQUENCE: 1

```
gga aga cac tgg aac ttg tta gcc gtt ttg tgc gcc ata gca atc tct       48
Gly Arg His Trp Asn Leu Leu Ala Val Leu Cys Ala Ile Ala Ile Ser
 1               5                  10                  15 tca att aat aca gtt gaa gca tca gac cag aag gcc agg ata gta tgt       96
Ser Ile Asn Thr Val Glu Ala Ser Asp Gln Lys Ala Arg Ile Val Cys
             20                  25                  30 tac ttc agc aat tgg gca gtt tac agg ccc gga ata ggc aga tat ggc      144
Tyr Phe Ser Asn Trp Ala Val Tyr Arg Pro Gly Ile Gly Arg Tyr Gly
         35                  40                  45 ata gag gac ata cca gtt gac ttg tgt acc cat ata gtt tat tct ttc      192
Ile Glu Asp Ile Pro Val Asp Leu Cys Thr His Ile Val Tyr Ser Phe
     50                  55                  60 atc gga gta gac gac aaa gac tgg agc gtg ctg gtc atc gac cca gag      240
Ile Gly Val Asp Asp Lys Asp Trp Ser Val Leu Val Ile Asp Pro Glu
 65                  70                  75                  80 ttg gac ata gat gac aat ggt ttc aag aat ttc aca aat ttg aga aaa      288
Leu Asp Ile Asp Asp Asn Gly Phe Lys Asn Phe Thr Asn Leu Arg Lys
                 85                  90                  95 att cat cca aat gtg aaa tta caa ata gcc gtc gga gga tgg gct gaa      336
Ile His Pro Asn Val Lys Leu Gln Ile Ala Val Gly Gly Trp Ala Glu
            100                 105                 110 ggc gga aaa aaa tat tcg acc atg gtg gcc gaa aag agg aag aga tca      384
Gly Gly Lys Lys Tyr Ser Thr Met Val Ala Glu Lys Arg Lys Arg Ser
        115                 120                 125 gcc ttt att cgc agt gta gtt gat ttc atg aac gaa tac aag ttc gac      432
Ala Phe Ile Arg Ser Val Val Asp Phe Met Asn Glu Tyr Lys Phe Asp
    130                 135                 140 ggt ttc gac ttg gat tgg gag tat cct ggt gct gct gat aga ggt ggc      480
Gly Phe Asp Leu Asp Trp Glu Tyr Pro Gly Ala Ala Asp Arg Gly Gly
145                 150                 155                 160 agt ttt tcc gac aaa gac aaa ttt tta tac ttt gtc caa gaa ttg cga      528
Ser Phe Ser Asp Lys Asp Lys Phe Leu Tyr Phe Val Gln Glu Leu Arg
                165                 170                 175 agg gct ttc aac aaa caa ggc aaa aac tgg gag atc acc atg gct gtc      576
Arg Ala Phe Asn Lys Gln Gly Lys Asn Trp Glu Ile Thr Met Ala Val
            180                 185                 190 ccg att gcc aaa ttt agg ctg cag gaa gga tat cat gta cca gaa ctt      624
Pro Ile Ala Lys Phe Arg Leu Gln Glu Gly Tyr His Val Pro Glu Leu
        195                 200                 205 tgc gaa tta tta gat gct atc cac gta atg tct tac gat ttg aga gga      672
Cys Glu Leu Leu Asp Ala Ile His Val Met Ser Tyr Asp Leu Arg Gly
    210                 215                 220 aat tgg gca ggg ttt gct gat acc cac agt ccc ttg tac aga agg cca      720
Asn Trp Ala Gly Phe Ala Asp Thr His Ser Pro Leu Tyr Arg Arg Pro
```

-continued

```
               225                 230                 235                 240
cat gat caa tat gct tat gag aaa ctc aat gtg aat gat gga tta caa        768
His Asp Gln Tyr Ala Tyr Glu Lys Leu Asn Val Asn Asp Gly Leu Gln
                    245                 250                 255 tta tgg gtt gat atg ggt tgt cca gca aac aag ttg gtc gtt ggt gtt        816
Leu Trp Val Asp Met Gly Cys Pro Ala Asn Lys Leu Val Val Gly Val
                260                 265                 270 cca ttt tat gga aga tcc ttc aca ttg agc aac agc aat aag gac tac        864
Pro Phe Tyr Gly Arg Ser Phe Thr Leu Ser Asn Ser Asn Lys Asp Tyr
            275                 280                 285 agg ttg gga acc tac atc aac aaa gaa gct gga gga ggt gaa cct gga        912
Arg Leu Gly Thr Tyr Ile Asn Lys Glu Ala Gly Gly Gly Glu Pro Gly
        290                 295                 300 cct tac act aac gct acc gga ttt att tct tat tat gag ata tgc tta        960
Pro Tyr Thr Asn Ala Thr Gly Phe Ile Ser Tyr Tyr Glu Ile Cys Leu
305                 310                 315                 320 gaa gtt gat gat cct tcc aaa ggc tgg act aaa aaa tgg gac gaa cat       1008
Glu Val Asp Asp Pro Ser Lys Gly Trp Thr Lys Lys Trp Asp Glu His
                    325                 330                 335 gga aaa gtg cca tat gct tat aaa gga aat caa tgg gtt ggc tac gaa       1056
Gly Lys Val Pro Tyr Ala Tyr Lys Gly Asn Gln Trp Val Gly Tyr Glu
                340                 345                 350 gac cca aaa tcc gtg gct ctg aag atg gaa ttt att aaa tct aag ggt       1104
Asp Pro Lys Ser Val Ala Leu Lys Met Glu Phe Ile Lys Ser Lys Gly
            355                 360                 365 tat gga ggt gcc atg act tgg gcc atc gac atg gac gat ttc caa gga       1152
Tyr Gly Gly Ala Met Thr Trp Ala Ile Asp Met Asp Asp Phe Gln Gly
        370                 375                 380 gta tgc tct gat gac aaa cac acc ttg gcg gtc atc atg cac gat tac       1200
Val Cys Ser Asp Asp Lys His Thr Leu Ala Val Ile Met His Asp Tyr
385                 390                 395                 400 atg aag aat tat att gtt cct gaa ttt gat tcg agt cgg att act ccc       1248
Met Lys Asn Tyr Ile Val Pro Glu Phe Asp Ser Ser Arg Ile Thr Pro
                    405                 410                 415 agg cct gaa tgg gca aaa cca cca agc act cct tca caa gaa cca gac       1296
Arg Pro Glu Trp Ala Lys Pro Pro Ser Thr Pro Ser Gln Glu Pro Asp
                420                 425                 430 gac aca cca tac att ccc aca acc cac gca cca aaa ccg agc cgc aaa       1344
Asp Thr Pro Tyr Ile Pro Thr Thr His Ala Pro Lys Pro Ser Arg Lys
            435                 440                 445 cca acc aga aaa ccg aaa cca aca acc aca act gtg gcg gca acc act       1392
Pro Thr Arg Lys Pro Lys Pro Thr Thr Thr Val Ala Ala Thr Thr
        450                 455                 460 cct gtt gcc aca acg act aca gaa cac cat cac cac cat cac gaa gaa       1440
Pro Val Ala Thr Thr Thr Thr Glu His His His His His His Glu Glu
465                 470                 475                 480 gag aag ccg agc gaa cag gac aac caa gtt ggt agc caa gat act act       1488
Glu Lys Pro Ser Glu Gln Asp Asn Gln Val Gly Ser Gln Asp Thr Thr
                    485                 490                 495 gca act gat gta gat tgt tcg cag gaa gac tat ttg cct cat gag gat       1536
Ala Thr Asp Val Asp Cys Ser Gln Glu Asp Tyr Leu Pro His Glu Asp
                500                 505                 510 tgc aac aag tat tac cgt tgt gtc cac gga gaa gca gtt ctc ttc act       1584
Cys Asn Lys Tyr Tyr Arg Cys Val His Gly Glu Ala Val Leu Phe Thr
            515                 520                 525 tgt cga gaa gga acc gtt tac cac acc ata agc cac gtt tgt gat tgg       1632
Cys Arg Glu Gly Thr Val Tyr His Thr Ile Ser His Val Cys Asp Trp
        530                 535                 540 gca tcg aat tca gac aga gaa aga tgt cga gac tta aaa agc gtt cca       1680
```

-continued

| | | | | | | | | | | | | | |
|---|---|---|---|---|---|---|---|---|---|---|---|---|---|
| Ala | Ser | Asn | Ser | Asp | Arg | Glu | Arg | Cys | Arg | Asp | Leu | Lys | Ser | Val | Pro |
| 545 | | | | 550 | | | | | 555 | | | | | 560 | cct cca aaa tta ttg act gat gaa gaa ata gct aat aaa cta tcg aaa   1728
Pro Pro Lys Leu Leu Thr Asp Glu Glu Ile Ala Asn Lys Leu Ser Lys
                        565                    570                  575 tat att gac tta cct ata ttg taattataga aatatgtact ggtgtcgaag   1779
Tyr Ile Asp Leu Pro Ile Leu
                        580 gaatgattgg aaggaattca gagacagaga ccctattggt ttcaaggacc aacattaaat   1839
gacagcatct ttagtcacca acagtattta tatgacgatt tgtctgtata atttatttta   1899
ttttattccc ctaaatagtt aacttgattg tagcttggaa tttcctaaat aaagaagatt   1959
catgtgtgat gagccagtta actgttattg acaaatattg gcaaagtggc agactttgt   2019
gtattgacga ttatactcgt catgcatatt aatctttgac cattagctat ttgaattgca   2079
acctttaagt cataatttca aaatcaagg catttagaat actttaaagc tctgccgaaa   2139
taaaaaatt gttgtaagta gcattttacc tcaaaccaa cattatacct ctattctgag   2199
gacatacatg acattgatat gtgtgcagac tatgcacaca gatcaatgat tacgccacag   2259
ttaactggtt aataagttat agattttcaa atgaagcatt agaatgactg gccaataatg   2319
tcttcccata tttttttaa caaattgaga atataaaaaa taatttgtca tttataatgc   2379
atttcagtac tagtatatcc taagtataaa ttttttttgtt tgtttattta tttaagttta   2439
ttaggtccta caaatatgat actcaaatat ttataaacgt tgtagaaaaa tatgaaattg   2499
tacgtgataa gaattttgga tttgtaatta tttatattaa taataaaata gaataaaaac   2559
gaaaaaaaaa aaaaaaaaaa aaaaaaaaaa aaaaaaaaa aaaaaaaaaa a   2610

<210> SEQ ID NO 2
<211> LENGTH: 583
<212> TYPE: PRT
<213> ORGANISM: Ctenocephalides felis

<400> SEQUENCE: 2

| Gly | Arg | His | Trp | Asn | Leu | Leu | Ala | Val | Leu | Cys | Ala | Ile | Ala | Ile | Ser |
|---|---|---|---|---|---|---|---|---|---|---|---|---|---|---|---|
| 1 | | | | 5 | | | | | 10 | | | | | 15 | |

| Ser | Ile | Asn | Thr | Val | Glu | Ala | Ser | Asp | Gln | Lys | Ala | Arg | Ile | Val | Cys |
|---|---|---|---|---|---|---|---|---|---|---|---|---|---|---|---|
| | | | 20 | | | | | 25 | | | | | 30 | | |

| Tyr | Phe | Ser | Asn | Trp | Ala | Val | Tyr | Arg | Pro | Gly | Ile | Gly | Arg | Tyr | Gly |
|---|---|---|---|---|---|---|---|---|---|---|---|---|---|---|---|
| | | 35 | | | | | 40 | | | | | 45 | | | |

| Ile | Glu | Asp | Ile | Pro | Val | Asp | Leu | Cys | Thr | His | Ile | Val | Tyr | Ser | Phe |
|---|---|---|---|---|---|---|---|---|---|---|---|---|---|---|---|
| | 50 | | | | | 55 | | | | | 60 | | | | |

| Ile | Gly | Val | Asp | Asp | Lys | Asp | Trp | Ser | Val | Leu | Val | Ile | Asp | Pro | Glu |
|---|---|---|---|---|---|---|---|---|---|---|---|---|---|---|---|
| 65 | | | | | 70 | | | | | 75 | | | | | 80 |

| Leu | Asp | Ile | Asp | Asp | Asn | Gly | Phe | Lys | Asn | Phe | Thr | Asn | Leu | Arg | Lys |
|---|---|---|---|---|---|---|---|---|---|---|---|---|---|---|---|
| | | | | 85 | | | | | 90 | | | | | 95 | |

| Ile | His | Pro | Asn | Val | Lys | Leu | Gln | Ile | Ala | Val | Gly | Gly | Trp | Ala | Glu |
|---|---|---|---|---|---|---|---|---|---|---|---|---|---|---|---|
| | | | 100 | | | | | 105 | | | | | 110 | | |

| Gly | Gly | Lys | Lys | Tyr | Ser | Thr | Met | Val | Ala | Glu | Lys | Arg | Lys | Arg | Ser |
|---|---|---|---|---|---|---|---|---|---|---|---|---|---|---|---|
| | | 115 | | | | | 120 | | | | | 125 | | | |

| Ala | Phe | Ile | Arg | Ser | Val | Val | Asp | Phe | Met | Asn | Glu | Tyr | Lys | Phe | Asp |
|---|---|---|---|---|---|---|---|---|---|---|---|---|---|---|---|
| | 130 | | | | | 135 | | | | | 140 | | | | |

| Gly | Phe | Asp | Leu | Asp | Trp | Glu | Tyr | Pro | Gly | Ala | Ala | Asp | Arg | Gly | Gly |
|---|---|---|---|---|---|---|---|---|---|---|---|---|---|---|---|
| 145 | | | | | 150 | | | | | 155 | | | | | 160 |

| Ser | Phe | Ser | Asp | Lys | Asp | Lys | Phe | Leu | Tyr | Phe | Val | Gln | Glu | Leu | Arg |
|---|---|---|---|---|---|---|---|---|---|---|---|---|---|---|---|
| | | | | 165 | | | | | 170 | | | | | 175 | |

-continued

```
Arg Ala Phe Asn Lys Gln Gly Lys Asn Trp Glu Ile Thr Met Ala Val
            180                 185                 190
Pro Ile Ala Lys Phe Arg Leu Gln Glu Gly Tyr His Val Pro Glu Leu
            195                 200                 205
Cys Glu Leu Leu Asp Ala Ile His Val Met Ser Tyr Asp Leu Arg Gly
            210                 215                 220
Asn Trp Ala Gly Phe Ala Asp Thr His Ser Pro Leu Tyr Arg Arg Pro
225                 230                 235                 240
His Asp Gln Tyr Ala Tyr Glu Lys Leu Asn Val Asn Asp Gly Leu Gln
            245                 250                 255
Leu Trp Val Asp Met Gly Cys Pro Ala Asn Lys Leu Val Val Gly Val
            260                 265                 270
Pro Phe Tyr Gly Arg Ser Phe Thr Leu Ser Asn Ser Asn Lys Asp Tyr
            275                 280                 285
Arg Leu Gly Thr Tyr Ile Asn Lys Glu Ala Gly Gly Gly Glu Pro Gly
            290                 295                 300
Pro Tyr Thr Asn Ala Thr Gly Phe Ile Ser Tyr Tyr Glu Ile Cys Leu
305                 310                 315                 320
Glu Val Asp Asp Pro Ser Lys Gly Trp Thr Lys Lys Trp Asp Glu His
            325                 330                 335
Gly Lys Val Pro Tyr Ala Tyr Lys Gly Asn Gln Trp Val Gly Tyr Glu
            340                 345                 350
Asp Pro Lys Ser Val Ala Leu Lys Met Glu Phe Ile Lys Ser Lys Gly
            355                 360                 365
Tyr Gly Gly Ala Met Thr Trp Ala Ile Asp Met Asp Asp Phe Gln Gly
            370                 375                 380
Val Cys Ser Asp Asp Lys His Thr Leu Ala Val Ile Met His Asp Tyr
385                 390                 395                 400
Met Lys Asn Tyr Ile Val Pro Glu Phe Asp Ser Ser Arg Ile Thr Pro
            405                 410                 415
Arg Pro Glu Trp Ala Lys Pro Ser Thr Pro Ser Gln Glu Pro Asp
            420                 425                 430
Asp Thr Pro Tyr Ile Pro Thr Thr His Ala Pro Lys Pro Ser Arg Lys
            435                 440                 445
Pro Thr Arg Lys Pro Lys Pro Thr Thr Thr Val Ala Ala Thr Thr
450                 455                 460
Pro Val Ala Thr Thr Thr Thr Glu His His His His His His Glu Glu
465                 470                 475                 480
Glu Lys Pro Ser Glu Gln Asp Asn Gln Val Gly Ser Gln Asp Thr Thr
            485                 490                 495
Ala Thr Asp Val Asp Cys Ser Gln Glu Asp Tyr Leu Pro His Glu Asp
            500                 505                 510
Cys Asn Lys Tyr Tyr Arg Cys Val His Gly Glu Ala Val Leu Phe Thr
            515                 520                 525
Cys Arg Glu Gly Thr Val Tyr His Thr Ile Ser His Val Cys Asp Trp
            530                 535                 540
Ala Ser Asn Ser Asp Arg Glu Arg Cys Arg Asp Leu Lys Ser Val Pro
545                 550                 555                 560
Pro Pro Lys Leu Leu Thr Asp Glu Glu Ile Ala Asn Lys Leu Ser Lys
            565                 570                 575
Tyr Ile Asp Leu Pro Ile Leu
            580
```

<210> SEQ ID NO 3
<211> LENGTH: 2610
<212> TYPE: DNA
<213> ORGANISM: Ctenocephalides felis

<400> SEQUENCE: 3

```
tttttttttt tttttttttt tttttttttt tttttttttt tttttttttt cgtttttatt      60
ctattttatt attaatataa ataattacaa atccaaaatt cttatcacgt acaatttcat     120
attttctac aacgtttata aatatttgag tatcatattt gtaggaccta ataaacttaa     180
ataaataaac aaacaaaaaa atttatactt aggatatact agtactgaaa tgcattataa     240
atgacaaatt attttttata ttctcaattt gttaaaaaaa atatgggaag acattattgg     300
ccagtcattc taatgcttca tttgaaaatc tataacttat taaccagtta actgtggcgt     360
aatcattgat ctgtgtgcat agtctgcaca catatcaatg tcatgtatgt cctcagaata     420
gaggtataat gttggttttg aggtaaaatg ctacttacaa caattttttt atttcggcag     480
agctttaaag tattctaaat gccttgattt ttgaaattat gacttaaagg ttgcaattca     540
aatagctaat ggtcaaagat taatatgcat gacgagtata atcgtcaata cacaaaagtc     600
tgccactttg ccaatatttg tcaataacag ttaactggct catcacacat gaatcttctt     660
tatttaggaa attccaagct acaatcaagt taactattta ggggaataaa ataaaataaa     720
ttatacagac aaatcgtcat ataaatactg ttggtgacta agatgctgt catttaatgt     780
tggtccttga accaataggg gtctctgtct ctgaattcct tccaatcatt ccttcgacac     840
cagtacatat ttctataatt acaatatagg taagtcaata tatttcgata gtttattagc     900
tatttcttca tcagtcaata attttggagg tggaacgctt tttaagtctc gacatctttc     960
tctgtctgaa ttcgatgccc aatcacaaac gtggcttatg gtgtggtaaa cggttccttc    1020
tcgacaagtg aagagaactg cttctccgtg gacacaacgg taatacttgt tgcaatcctc    1080
atgaggcaaa tagtcttcct gcgaacaatc tacatcagtt gcagtagtat cttggctacc    1140
aacttggttg tcctgttcgc tcggcttctc ttcttcgtga tggtggtgat ggtgttctgt    1200
agtcgttgtg gcaacaggag tggttgccgc acagttgtg gttgttggtt tcggttttct    1260
ggttggtttg cggctcggtt ttggtgcgtg gttgtggga atgtatggtg tgtcgtctgg    1320
ttcttgtgaa ggagtgcttg gtggttttgc ccattcaggc ctgggagtaa tccgactcga    1380
atcaaattca ggaacaatat aattcttcat gtaatcgtgc atgatgaccg ccaaggtgtg    1440
tttgtcatca gagcatactc cttggaaatc gtccatgtcg atgcccaag tcatggcacc    1500
tccataaccc ttagatttaa taaattccat cttcagagcc acggattttg ggtcttcgta    1560
gccaacccat tgatttcctt tataagcata tggcactttt ccatgttcgt cccatttttt    1620
agtccagcct ttggaaggat catcaacttc taagcatatc tcataataag aaataaatcc    1680
ggtagcgtta gtgtaaggtc caggttcacc tcctccagct tctttgttga tgtaggttcc    1740
caacctgtag tccttattgc tgttgctcaa tgtgaaggat cttccataaa atggaacacc    1800
aacgaccaac ttgtttgctg acaacccat atcaacccat aattgtaatc catcattcac    1860
attgagtttc tcataagcat attgatcatg tggccttctg tacaagggac tgtgggtatc    1920
agcaaaccct gcccaatttc ctctcaaatc gtaagacatt acgtggatag catctaataa    1980
ttcgcaaagt tctggtacat gatatccttc ctgcagccta aatttggcaa tcgggacagc    2040
catggtgatc tcccagtttt tgccttgttt gttgaaagcc cttcgcaatt cttggacaaa    2100
gtataaaaat ttgtctttgt cggaaaaaact gccacctcta tcagcagcac caggatactc    2160
```

-continued

```
ccaatccaag tcgaaaccgt cgaacttgta ttcgttcatg aaatcaacta cactgcgaat    2220
aaaggctgat ctcttcctct tttcggccac catggtcgaa tattttttc cgccttcagc     2280 ccatcctccg acggctattt gtaatttcac atttggatga attttctca aatttgtgaa     2340 attcttgaaa ccattgtcat ctatgtccaa ctctgggtcg atgaccagca cgctccagtc    2400
tttgtcgtct actccgatga aagaataaac tatatgggta cacaagtcaa ctggtatgtc    2460
ctctatgcca tatctgccta ttccgggcct gtaaactgcc caattgctga agtaacatac    2520
tatcctggcc ttctggtctg atgcttcaac tgtattaatt gaagagattg ctatggcgca    2580
caaaacggct aacaagttcc agtgtcttcc                                     2610
```

```
<210> SEQ ID NO 4
<211> LENGTH: 1749
<212> TYPE: DNA
<213> ORGANISM: Ctenocephalides felis
<220> FEATURE:
<221> NAME/KEY: CDS
<222> LOCATION: (1)..(1749)

<400> SEQUENCE: 4
```

| | | | | | | | | | | | | | | | | |
|---|---|---|---|---|---|---|---|---|---|---|---|---|---|---|---|---|
| gga | aga | cac | tgg | aac | ttg | tta | gcc | gtt | ttg | tgc | gcc | ata | gca | atc | tct | 48 |
| Gly | Arg | His | Trp | Asn | Leu | Leu | Ala | Val | Leu | Cys | Ala | Ile | Ala | Ile | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tca | att | aat | aca | gtt | gaa | gca | tca | gac | cag | aag | gcc | agg | ata | gta | tgt | 96 |
| Ser | Ile | Asn | Thr | Val | Glu | Ala | Ser | Asp | Gln | Lys | Ala | Arg | Ile | Val | Cys | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | ttc | agc | aat | tgg | gca | gtt | tac | agg | ccc | gga | ata | ggc | aga | tat | ggc | 144 |
| Tyr | Phe | Ser | Asn | Trp | Ala | Val | Tyr | Arg | Pro | Gly | Ile | Gly | Arg | Tyr | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| ata | gag | gac | ata | cca | gtt | gac | ttg | tgt | acc | cat | ata | gtt | tat | tct | ttc | 192 |
| Ile | Glu | Asp | Ile | Pro | Val | Asp | Leu | Cys | Thr | His | Ile | Val | Tyr | Ser | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | gga | gta | gac | gac | aaa | gac | tgg | agc | gtg | ctg | gtc | atc | gac | cca | gag | 240 |
| Ile | Gly | Val | Asp | Asp | Lys | Asp | Trp | Ser | Val | Leu | Val | Ile | Asp | Pro | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttg | gac | ata | gat | gac | aat | ggt | ttc | aag | aat | ttc | aca | aat | ttg | aga | aaa | 288 |
| Leu | Asp | Ile | Asp | Asp | Asn | Gly | Phe | Lys | Asn | Phe | Thr | Asn | Leu | Arg | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| att | cat | cca | aat | gtg | aaa | tta | caa | ata | gcc | gtc | gga | gga | tgg | gct | gaa | 336 |
| Ile | His | Pro | Asn | Val | Lys | Leu | Gln | Ile | Ala | Val | Gly | Gly | Trp | Ala | Glu | |
| | | | | 100 | | | | | 105 | | | | | 110 | | |

| | | | | | | | | | | | | | | | | |
|---|---|---|---|---|---|---|---|---|---|---|---|---|---|---|---|---|
| ggc | gga | aaa | aaa | tat | tcg | acc | atg | gtg | gcc | gaa | aag | agg | aag | aga | tca | 384 |
| Gly | Gly | Lys | Lys | Tyr | Ser | Thr | Met | Val | Ala | Glu | Lys | Arg | Lys | Arg | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | ttt | att | cgc | agt | gta | gtt | gat | ttc | atg | aac | gaa | tac | aag | ttc | gac | 432 |
| Ala | Phe | Ile | Arg | Ser | Val | Val | Asp | Phe | Met | Asn | Glu | Tyr | Lys | Phe | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| ggt | ttc | gac | ttg | gat | tgg | gag | tat | cct | ggt | gct | gct | gat | aga | ggt | ggc | 480 |
| Gly | Phe | Asp | Leu | Asp | Trp | Glu | Tyr | Pro | Gly | Ala | Ala | Asp | Arg | Gly | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | ttt | tcc | gac | aaa | gac | aaa | ttt | tta | tac | ttt | gtc | caa | gaa | ttg | cga | 528 |
| Ser | Phe | Ser | Asp | Lys | Asp | Lys | Phe | Leu | Tyr | Phe | Val | Gln | Glu | Leu | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| agg | gct | ttc | aac | aaa | caa | ggc | aaa | aac | tgg | gag | atc | acc | atg | gct | gtc | 576 |
| Arg | Ala | Phe | Asn | Lys | Gln | Gly | Lys | Asn | Trp | Glu | Ile | Thr | Met | Ala | Val | |
| | | | | 180 | | | | | 185 | | | | | 190 | | |

| | | | | | | | | | | | | | | | | |
|---|---|---|---|---|---|---|---|---|---|---|---|---|---|---|---|---|
| ccg | att | gcc | aaa | ttt | agg | ctg | cag | gaa | gga | tat | cat | gta | cca | gaa | ctt | 624 |
| Pro | Ile | Ala | Lys | Phe | Arg | Leu | Gln | Glu | Gly | Tyr | His | Val | Pro | Glu | Leu | |
| | | | 195 | | | | | 200 | | | | | 205 | | | |

```
tgc gaa tta tta gat gct atc cac gta atg tct tac gat ttg aga gga    672
Cys Glu Leu Leu Asp Ala Ile His Val Met Ser Tyr Asp Leu Arg Gly
    210                 215                 220 aat tgg gca ggg ttt gct gat acc cac agt ccc ttg tac aga agg cca    720
Asn Trp Ala Gly Phe Ala Asp Thr His Ser Pro Leu Tyr Arg Arg Pro
225                 230                 235                 240 cat gat caa tat gct tat gag aaa ctc aat gtg aat gat gga tta caa    768
His Asp Gln Tyr Ala Tyr Glu Lys Leu Asn Val Asn Asp Gly Leu Gln
                245                 250                 255 tta tgg gtt gat atg ggt tgt cca gca aac aag ttg gtc gtt ggt gtt    816
Leu Trp Val Asp Met Gly Cys Pro Ala Asn Lys Leu Val Val Gly Val
            260                 265                 270 cca ttt tat gga aga tcc ttc aca ttg agc aac agc aat aag gac tac    864
Pro Phe Tyr Gly Arg Ser Phe Thr Leu Ser Asn Ser Asn Lys Asp Tyr
        275                 280                 285 agg ttg gga acc tac atc aac aaa gaa gct gga gga ggt gaa cct gga    912
Arg Leu Gly Thr Tyr Ile Asn Lys Glu Ala Gly Gly Gly Glu Pro Gly
    290                 295                 300 cct tac act aac gct acc gga ttt att tct tat tat gag ata tgc tta    960
Pro Tyr Thr Asn Ala Thr Gly Phe Ile Ser Tyr Tyr Glu Ile Cys Leu
305                 310                 315                 320 gaa gtt gat gat cct tcc aaa ggc tgg act aaa aaa tgg gac gaa cat   1008
Glu Val Asp Asp Pro Ser Lys Gly Trp Thr Lys Lys Trp Asp Glu His
                325                 330                 335 gga aaa gtg cca tat gct tat aaa gga aat caa tgg gtt ggc tac gaa   1056
Gly Lys Val Pro Tyr Ala Tyr Lys Gly Asn Gln Trp Val Gly Tyr Glu
            340                 345                 350 gac cca aaa tcc gtg gct ctg aag atg gaa ttt att aaa tct aag ggt   1104
Asp Pro Lys Ser Val Ala Leu Lys Met Glu Phe Ile Lys Ser Lys Gly
        355                 360                 365 tat gga ggt gcc atg act tgg gcc atc gac atg gac gat ttc caa gga   1152
Tyr Gly Gly Ala Met Thr Trp Ala Ile Asp Met Asp Asp Phe Gln Gly
    370                 375                 380 gta tgc tct gat gac aaa cac acc ttg gcg gtc atc atg cac gat tac   1200
Val Cys Ser Asp Asp Lys His Thr Leu Ala Val Ile Met His Asp Tyr
385                 390                 395                 400 atg aag aat tat att gtt cct gaa ttt gat tcg agt cgg att act ccc   1248
Met Lys Asn Tyr Ile Val Pro Glu Phe Asp Ser Ser Arg Ile Thr Pro
                405                 410                 415 agg cct gaa tgg gca aaa cca cca agc act cct tca caa gaa cca gac   1296
Arg Pro Glu Trp Ala Lys Pro Pro Ser Thr Pro Ser Gln Glu Pro Asp
            420                 425                 430 gac aca cca tac att ccc aca acc cac gca cca aaa ccg agc cgc aaa   1344
Asp Thr Pro Tyr Ile Pro Thr Thr His Ala Pro Lys Pro Ser Arg Lys
        435                 440                 445 cca acc aga aaa ccg aaa cca aca acc aca act gtg gcg gca acc act   1392
Pro Thr Arg Lys Pro Lys Pro Thr Thr Thr Thr Val Ala Ala Thr Thr
    450                 455                 460 cct gtt gcc aca acg act aca gaa cac cat cac cac cat cac gaa gaa   1440
Pro Val Ala Thr Thr Thr Thr Glu His His His His His His Glu Glu
465                 470                 475                 480 gag aag ccg agc gaa cag gac aac caa gtt ggt agc caa gat act act   1488
Glu Lys Pro Ser Glu Gln Asp Asn Gln Val Gly Ser Gln Asp Thr Thr
                485                 490                 495 gca act gat gta gat tgt tcg cag gaa gac tat ttg cct cat gag gat   1536
Ala Thr Asp Val Asp Cys Ser Gln Glu Asp Tyr Leu Pro His Glu Asp
            500                 505                 510 tgc aac aag tat tac cgt tgt gtc cac gga gaa gca gtt ctc ttc act   1584
Cys Asn Lys Tyr Tyr Arg Cys Val His Gly Glu Ala Val Leu Phe Thr
```

-continued

```
                515                 520                 525
tgt cga gaa gga acc gtt tac cac acc ata agc cac gtt tgt gat tgg     1632
Cys Arg Glu Gly Thr Val Tyr His Thr Ile Ser His Val Cys Asp Trp
    530                 535                 540 gca tcg aat tca gac aga gaa aga tgt cga gac tta aaa agc gtt cca     1680
Ala Ser Asn Ser Asp Arg Glu Arg Cys Arg Asp Leu Lys Ser Val Pro
545                 550                 555                 560 cct cca aaa tta ttg act gat gaa gaa ata gct aat aaa cta tcg aaa     1728
Pro Pro Lys Leu Leu Thr Asp Glu Glu Ile Ala Asn Lys Leu Ser Lys
                565                 570                 575 tat att gac tta cct ata ttg                                         1749
Tyr Ile Asp Leu Pro Ile Leu
            580
```

<210> SEQ ID NO 5
<211> LENGTH: 583
<212> TYPE: PRT
<213> ORGANISM: Ctenocephalides felis

<400> SEQUENCE: 5

```
Gly Arg His Trp Asn Leu Leu Ala Val Leu Cys Ala Ile Ala Ile Ser
 1               5                  10                  15

Ser Ile Asn Thr Val Glu Ala Ser Asp Gln Lys Ala Arg Ile Val Cys
            20                  25                  30

Tyr Phe Ser Asn Trp Ala Val Tyr Arg Pro Gly Ile Gly Arg Tyr Gly
        35                  40                  45

Ile Glu Asp Ile Pro Val Asp Leu Cys Thr His Ile Val Tyr Ser Phe
    50                  55                  60

Ile Gly Val Asp Asp Lys Asp Trp Ser Val Leu Val Ile Asp Pro Glu
65                  70                  75                  80

Leu Asp Ile Asp Asp Asn Gly Phe Lys Asn Phe Thr Asn Leu Arg Lys
                85                  90                  95

Ile His Pro Asn Val Lys Leu Gln Ile Ala Val Gly Gly Trp Ala Glu
            100                 105                 110

Gly Gly Lys Lys Tyr Ser Thr Met Val Ala Glu Lys Lys Arg Ser
        115                 120                 125

Ala Phe Ile Arg Ser Val Val Asp Phe Met Asn Glu Tyr Lys Phe Asp
    130                 135                 140

Gly Phe Asp Leu Asp Trp Glu Tyr Pro Gly Ala Ala Asp Arg Gly Gly
145                 150                 155                 160

Ser Phe Ser Asp Lys Asp Lys Phe Leu Tyr Phe Val Gln Glu Leu Arg
                165                 170                 175

Arg Ala Phe Asn Lys Gln Gly Lys Asn Trp Glu Ile Thr Met Ala Val
            180                 185                 190

Pro Ile Ala Lys Phe Arg Leu Gln Glu Gly Tyr His Val Pro Glu Leu
        195                 200                 205

Cys Glu Leu Leu Asp Ala Ile His Val Met Ser Tyr Asp Leu Arg Gly
    210                 215                 220

Asn Trp Ala Gly Phe Ala Asp Thr His Ser Pro Leu Tyr Arg Arg Pro
225                 230                 235                 240

His Asp Gln Tyr Ala Tyr Glu Lys Leu Asn Val Asn Asp Gly Leu Gln
                245                 250                 255

Leu Trp Val Asp Met Gly Cys Pro Ala Asn Lys Leu Val Val Gly Val
            260                 265                 270

Pro Phe Tyr Gly Arg Ser Phe Thr Leu Ser Asn Ser Asn Lys Asp Tyr
        275                 280                 285
```

-continued

```
Arg Leu Gly Thr Tyr Ile Asn Lys Glu Ala Gly Gly Glu Pro Gly
    290                 295                 300
Pro Tyr Thr Asn Ala Thr Gly Phe Ile Ser Tyr Tyr Glu Ile Cys Leu
305                 310                 315                 320
Glu Val Asp Asp Pro Ser Lys Gly Trp Thr Lys Lys Trp Asp Glu His
                325                 330                 335
Gly Lys Val Pro Tyr Ala Tyr Lys Gly Asn Gln Trp Val Gly Tyr Glu
            340                 345                 350
Asp Pro Lys Ser Val Ala Leu Lys Met Glu Phe Ile Lys Ser Lys Gly
        355                 360                 365
Tyr Gly Gly Ala Met Thr Trp Ala Ile Asp Met Asp Asp Phe Gln Gly
    370                 375                 380
Val Cys Ser Asp Asp Lys His Thr Leu Ala Val Ile Met His Asp Tyr
385                 390                 395                 400
Met Lys Asn Tyr Ile Val Pro Glu Phe Asp Ser Ser Arg Ile Thr Pro
                405                 410                 415
Arg Pro Glu Trp Ala Lys Pro Pro Ser Thr Pro Ser Gln Glu Pro Asp
            420                 425                 430
Asp Thr Pro Tyr Ile Pro Thr Thr His Ala Pro Lys Pro Ser Arg Lys
        435                 440                 445
Pro Thr Arg Lys Pro Lys Pro Thr Thr Thr Val Ala Ala Thr Thr
    450                 455                 460
Pro Val Ala Thr Thr Thr Thr Glu His His His His His His Glu Glu
465                 470                 475                 480
Glu Lys Pro Ser Glu Gln Asp Asn Gln Val Gly Ser Gln Asp Thr Thr
                485                 490                 495
Ala Thr Asp Val Asp Cys Ser Gln Glu Asp Tyr Leu Pro His Glu Asp
            500                 505                 510
Cys Asn Lys Tyr Tyr Arg Cys Val His Gly Glu Ala Val Leu Phe Thr
        515                 520                 525
Cys Arg Glu Gly Thr Val Tyr His Thr Ile Ser His Val Cys Asp Trp
    530                 535                 540
Ala Ser Asn Ser Asp Arg Glu Arg Cys Arg Asp Leu Lys Ser Val Pro
545                 550                 555                 560
Pro Pro Lys Leu Leu Thr Asp Glu Glu Ile Ala Asn Lys Leu Ser Lys
                565                 570                 575
Tyr Ile Asp Leu Pro Ile Leu
            580

<210> SEQ ID NO 6
<211> LENGTH: 1749
<212> TYPE: DNA
<213> ORGANISM: Ctenocephalides felis

<400> SEQUENCE: 6
caatataggt aagtcaatat atttcgatag tttattagct atttcttcat cagtcaataa      60
ttttggaggt ggaacgcttt ttaagtctcg acatctttct ctgtctgaat tcgatgccca     120
atcacaaacg tggcttatgg tgtggtaaac ggttccttct cgacaagtga agagaactgc     180
ttctccgtgg acacaacggt aatacttgtt gcaatcctca tgaggcaaat agtcttcctg     240
cgaacaatct acatcagttg cagtagtatc ttggctacca acttggttgt cctgttcgct     300
cggcttctct tcttcgtgat ggtggtgatg gtgttctgta gtcgttgtgg caacaggagt     360
ggttgccgcc acagttgtgg ttgttggttt cggttttctg gttggtttgc ggctcggttt     420
```

-continued

```
tggtgcgtgg gttgtgggaa tgtatggtgt gtcgtctggt tcttgtgaag gagtgcttgg      480
tggttttgcc cattcaggcc tgggagtaat ccgactcgaa tcaaattcag gaacaatata      540
attcttcatg taatcgtgca tgatgaccgc caaggtgtgt tgtcatcag agcatactcc       600 ttggaaatcg tccatgtcga tggcccaagt catggcacct ccataaccct tagatttaat     660
aaattccatc ttcagagcca cggattttgg gtcttcgtag ccaacccatt gatttccttt     720
ataagcatat ggcacttttc catgttcgtc ccattttta gtccagcctt tggaaggatc      780
atcaacttct aagcatatct cataataaga aataaatccg gtagcgttag tgtaaggtcc     840
aggttcacct cctccagctt ctttgttgat gtaggttccc aacctgtagt ccttattgct     900
gttgctcaat gtgaaggatc ttccataaaa tggaacacca cgaccaact tgtttgctgg      960 acaacccata tcaacccata attgtaatcc atcattcaca ttgagtttct cataagcata    1020
ttgatcatgt ggccttctgt acaagggact gtgggtatca gcaaaccctg cccaatttcc    1080
tctcaaatcg taagacatta cgtggatagc atctaataat tcgcaaagtt ctggtacatg    1140
atatccttcc tgcagcctaa atttggcaat cgggacagcc atggtgatct cccagttttt    1200
gccttgtttg ttgaaagccc ttcgcaattc ttggacaaag tataaaaatt tgtctttgtc    1260
ggaaaaactg ccacctctat cagcagcacc aggatactcc caatccaagt cgaaaccgtc    1320
gaacttgtat tcgttcatga aatcaactac actgcgaata aaggctgatc tcttcctctt    1380
ttcggccacc atggtcgaat atttttttcc gccttcagcc catcctccga cggctatttg    1440
taatttcaca tttggatgaa tttttctcaa atttgtgaaa ttcttgaaac cattgtcatc    1500
tatgtccaac tctgggtcga tgaccagcac gctccagtct ttgtcgtcta ctccgatgaa    1560
agaataaact atatgggtac acaagtcaac tggtatgtcc tctatgccat atctgcctat    1620
tccgggcctg taaactgccc aattgctgaa gtaacatact atcctggcct tctggtctga    1680
tgcttcaact gtattaattg aagagattgc tatggcgcac aaaacggcta acaagttcca    1740
gtgtcttcc                                                             1749
```

<210> SEQ ID NO 7
<211> LENGTH: 405
<212> TYPE: DNA
<213> ORGANISM: Ctenocephalides felis
<220> FEATURE:
<221> NAME/KEY: CDS
<222> LOCATION: (55)..(405)

<400> SEQUENCE: 7

```
actcactata gggctcgagc ggccgcccgg gcaggttttt gtgtcgctgg aaac atg       57
                                                              Met
                                                               1 gga aga cac tgg aac ttg tta gcc gtt ttg tgc gcc atc gca atc tct      105
Gly Arg His Trp Asn Leu Leu Ala Val Leu Cys Ala Ile Ala Ile Ser
         5                  10                  15 tca att aat aca gtt gaa gct tca gac cag aag gcc agg ata gta tgt     153
Ser Ile Asn Thr Val Glu Ala Ser Asp Gln Lys Ala Arg Ile Val Cys
     20                  25                  30 tac ttc agc aat tgg gca gtt tac agg ccc gga ata ggc aga tat ggc     201
Tyr Phe Ser Asn Trp Ala Val Tyr Arg Pro Gly Ile Gly Arg Tyr Gly
 35                  40                  45 ata gaa gac ata cca gtt gac ttg tgt acc cat ata gtt tat tct ttc     249
Ile Glu Asp Ile Pro Val Asp Leu Cys Thr His Ile Val Tyr Ser Phe
 50                  55                  60                  65 atc gga gta gac gac aaa gac tgg agc gtg ctg gtc atc gac ccg gag     297
```

```
Ile Gly Val Asp Asp Lys Asp Trp Ser Val Leu Val Ile Asp Pro Glu
            70                  75                  80 ttg gac ata gat gac aat ggt ttt aag aat ttc aca aac ttg aga aaa    345
Leu Asp Ile Asp Asp Asn Gly Phe Lys Asn Phe Thr Asn Leu Arg Lys
                85                  90                  95 gcc cat cca aat gtt aaa tta caa ata gcc gtc gga gga tgg gct gaa    393
Ala His Pro Asn Val Lys Leu Gln Ile Ala Val Gly Gly Trp Ala Glu
            100                 105                 110 ggc gga aaa aaa                                                     405
Gly Gly Lys Lys
        115
```

<210> SEQ ID NO 8
<211> LENGTH: 117
<212> TYPE: PRT
<213> ORGANISM: Ctenocephalides felis

<400> SEQUENCE: 8

```
Met Gly Arg His Trp Asn Leu Leu Ala Val Leu Cys Ala Ile Ala Ile
 1               5                  10                  15

Ser Ser Ile Asn Thr Val Glu Ala Ser Asp Gln Lys Ala Arg Ile Val
            20                  25                  30

Cys Tyr Phe Ser Asn Trp Ala Val Tyr Arg Pro Gly Ile Gly Arg Tyr
        35                  40                  45

Gly Ile Glu Asp Ile Pro Val Asp Leu Cys Thr His Ile Val Tyr Ser
    50                  55                  60

Phe Ile Gly Val Asp Asp Lys Asp Trp Ser Val Leu Val Ile Asp Pro
65                  70                  75                  80

Glu Leu Asp Ile Asp Asp Asn Gly Phe Lys Asn Phe Thr Asn Leu Arg
                85                  90                  95

Lys Ala His Pro Asn Val Lys Leu Gln Ile Ala Val Gly Gly Trp Ala
            100                 105                 110

Glu Gly Gly Lys Lys
        115
```

<210> SEQ ID NO 9
<211> LENGTH: 405
<212> TYPE: DNA
<213> ORGANISM: Ctenocephalides felis

<400> SEQUENCE: 9

```
ttttttccg ccttcagccc atcctccgac ggctatttgt aatttaacat ttggatgggc     60
ttttctcaag tttgtgaaat tcttaaaacc attgtcatct atgtccaact ccgggtcgat    120
gaccagcacg ctccagtctt tgtcgtctac tccgatgaaa gaataaacta tgggtaca     180 caagtcaact ggtatgtctt ctatgccata tctgcctatt ccgggcctgt aaactgccca    240
attgctgaag taacatacta tcctggcctt ctggtctgaa gcttcaactg tattaattga    300
agagattgcg atggcgcaca aaacggctaa caagttccag tgtcttccca tgtttccagc    360
gacacaaaaa cctgcccggg cggccgctcg agccctatag tgagt                    405
```

<210> SEQ ID NO 10
<211> LENGTH: 351
<212> TYPE: DNA
<213> ORGANISM: Ctenocephalides felis
<220> FEATURE:
<221> NAME/KEY: CDS
<222> LOCATION: (1)..(351)

<400> SEQUENCE: 10

-continued

```
atg gga aga cac tgg aac ttg tta gcc gtt ttg tgc gcc atc gca atc    48
Met Gly Arg His Trp Asn Leu Leu Ala Val Leu Cys Ala Ile Ala Ile
 1               5                  10                  15 tct tca att aat aca gtt gaa gct tca gac cag aag gcc agg ata gta    96
Ser Ser Ile Asn Thr Val Glu Ala Ser Asp Gln Lys Ala Arg Ile Val
             20                  25                  30 tgt tac ttc agc aat tgg gca gtt tac agg ccc gga ata ggc aga tat   144
Cys Tyr Phe Ser Asn Trp Ala Val Tyr Arg Pro Gly Ile Gly Arg Tyr
         35                  40                  45 ggc ata gaa gac ata cca gtt gac ttg tgt acc cat ata gtt tat tct   192
Gly Ile Glu Asp Ile Pro Val Asp Leu Cys Thr His Ile Val Tyr Ser
 50                  55                  60 ttc atc gga gta gac gac aaa gac tgg agc gtg ctg gtc atc gac ccg   240
Phe Ile Gly Val Asp Asp Lys Asp Trp Ser Val Leu Val Ile Asp Pro
 65                  70                  75                  80 gag ttg gac ata gat gac aat ggt ttt aag aat ttc aca aac ttg aga   288
Glu Leu Asp Ile Asp Asp Asn Gly Phe Lys Asn Phe Thr Asn Leu Arg
                 85                  90                  95 aaa gcc cat cca aat gtt aaa tta caa ata gcc gtc gga gga tgg gct   336
Lys Ala His Pro Asn Val Lys Leu Gln Ile Ala Val Gly Gly Trp Ala
             100                 105                 110 gaa ggc gga aaa aaa                                                351
Glu Gly Gly Lys Lys
        115
```

<210> SEQ ID NO 11
<211> LENGTH: 117
<212> TYPE: PRT
<213> ORGANISM: Ctenocephalides felis

<400> SEQUENCE: 11

```
Met Gly Arg His Trp Asn Leu Leu Ala Val Leu Cys Ala Ile Ala Ile
 1               5                  10                  15

Ser Ser Ile Asn Thr Val Glu Ala Ser Asp Gln Lys Ala Arg Ile Val
             20                  25                  30

Cys Tyr Phe Ser Asn Trp Ala Val Tyr Arg Pro Gly Ile Gly Arg Tyr
         35                  40                  45

Gly Ile Glu Asp Ile Pro Val Asp Leu Cys Thr His Ile Val Tyr Ser
 50                  55                  60

Phe Ile Gly Val Asp Asp Lys Asp Trp Ser Val Leu Val Ile Asp Pro
 65                  70                  75                  80

Glu Leu Asp Ile Asp Asp Asn Gly Phe Lys Asn Phe Thr Asn Leu Arg
                 85                  90                  95

Lys Ala His Pro Asn Val Lys Leu Gln Ile Ala Val Gly Gly Trp Ala
             100                 105                 110

Glu Gly Gly Lys Lys
        115
```

<210> SEQ ID NO 12
<211> LENGTH: 351
<212> TYPE: DNA
<213> ORGANISM: Ctenocephalides felis

<400> SEQUENCE: 12

```
ttttttccg ccttcagccc atcctccgac ggctatttgt aatttaacat ttggatgggc    60
ttttctcaag tttgtgaaat tcttaaaacc attgtcatct atgtccaact ccgggtcgat   120
gaccagcacg ctccagtctt tgtcgtctac tccgatgaaa gaataaacta tatgggtaca   180
```

-continued

```
caagtcaact ggtatgtctt ctatgccata tctgcctatt ccgggcctgt aaactgccca      240
attgctgaag taacatacta tcctggcctt ctggtctgaa gcttcaactg tattaattga      300
agagattgcg atggcgcaca aaacggctaa caagttccag tgtcttccca t              351
```

```
<210> SEQ ID NO 13
<211> LENGTH: 1677
<212> TYPE: DNA
<213> ORGANISM: Ctenocephalides felis
<220> FEATURE:
<221> NAME/KEY: CDS
<222> LOCATION: (1)..(1677)

<400> SEQUENCE: 13
```

| | | | | | | | | | | | | | | | | |
|---|---|---|---|---|---|---|---|---|---|---|---|---|---|---|---|---|
| gac | cag | aag | gcc | agg | ata | gta | tgt | tac | ttc | agc | aat | tgg | gca | gtt | tac | 48 |
| Asp | Gln | Lys | Ala | Arg | Ile | Val | Cys | Tyr | Phe | Ser | Asn | Trp | Ala | Val | Tyr | |
| 1 | | | | 5 | | | | | 10 | | | | | 15 | | |
| agg | ccc | gga | ata | ggc | aga | tat | ggc | ata | gag | gac | ata | cca | gtt | gac | ttg | 96 |
| Arg | Pro | Gly | Ile | Gly | Arg | Tyr | Gly | Ile | Glu | Asp | Ile | Pro | Val | Asp | Leu | |
| | | | 20 | | | | | 25 | | | | | 30 | | | |
| tgt | acc | cat | ata | gtt | tat | tct | ttc | atc | gga | gta | gac | gac | aaa | gac | tgg | 144 |
| Cys | Thr | His | Ile | Val | Tyr | Ser | Phe | Ile | Gly | Val | Asp | Asp | Lys | Asp | Trp | |
| | | 35 | | | | | 40 | | | | | 45 | | | | |
| agc | gtg | ctg | gtc | atc | gac | cca | gag | ttg | gac | ata | gat | gac | aat | ggt | ttc | 192 |
| Ser | Val | Leu | Val | Ile | Asp | Pro | Glu | Leu | Asp | Ile | Asp | Asp | Asn | Gly | Phe | |
| | 50 | | | | | 55 | | | | | 60 | | | | | |
| aag | aat | ttc | aca | aat | ttg | aga | aaa | att | cat | cca | aat | gtg | aaa | tta | caa | 240 |
| Lys | Asn | Phe | Thr | Asn | Leu | Arg | Lys | Ile | His | Pro | Asn | Val | Lys | Leu | Gln | |
| 65 | | | | | 70 | | | | | 75 | | | | | 80 | |
| ata | gcc | gtc | gga | gga | tgg | gct | gaa | ggc | gga | aaa | aaa | tat | tcg | acc | atg | 288 |
| Ile | Ala | Val | Gly | Gly | Trp | Ala | Glu | Gly | Gly | Lys | Lys | Tyr | Ser | Thr | Met | |
| | | | | 85 | | | | | 90 | | | | | 95 | | |
| gtg | gcc | gaa | aag | agg | aag | aga | tca | gcc | ttt | att | cgc | agt | gta | gtt | gat | 336 |
| Val | Ala | Glu | Lys | Arg | Lys | Arg | Ser | Ala | Phe | Ile | Arg | Ser | Val | Val | Asp | |
| | | | 100 | | | | | 105 | | | | | 110 | | | |
| ttc | atg | aac | gaa | tac | aag | ttc | gac | ggt | ttc | gac | ttg | gat | tgg | gag | tat | 384 |
| Phe | Met | Asn | Glu | Tyr | Lys | Phe | Asp | Gly | Phe | Asp | Leu | Asp | Trp | Glu | Tyr | |
| | | 115 | | | | | 120 | | | | | 125 | | | | |
| cct | ggt | gct | gct | gat | aga | ggt | ggc | agt | ttt | tcc | gac | aaa | gac | aaa | ttt | 432 |
| Pro | Gly | Ala | Ala | Asp | Arg | Gly | Gly | Ser | Phe | Ser | Asp | Lys | Asp | Lys | Phe | |
| | 130 | | | | | 135 | | | | | 140 | | | | | |
| tta | tac | ttt | gtc | caa | gaa | ttg | cga | agg | gct | ttc | aac | aaa | caa | ggc | aaa | 480 |
| Leu | Tyr | Phe | Val | Gln | Glu | Leu | Arg | Arg | Ala | Phe | Asn | Lys | Gln | Gly | Lys | |
| 145 | | | | | 150 | | | | | 155 | | | | | 160 | |
| aac | tgg | gag | atc | acc | atg | gct | gtc | ccg | att | gcc | aaa | ttt | agg | ctg | cag | 528 |
| Asn | Trp | Glu | Ile | Thr | Met | Ala | Val | Pro | Ile | Ala | Lys | Phe | Arg | Leu | Gln | |
| | | | | 165 | | | | | 170 | | | | | 175 | | |
| gaa | gga | tat | cat | gta | cca | gaa | ctt | tgc | gaa | tta | tta | gat | gct | atc | cac | 576 |
| Glu | Gly | Tyr | His | Val | Pro | Glu | Leu | Cys | Glu | Leu | Leu | Asp | Ala | Ile | His | |
| | | | 180 | | | | | 185 | | | | | 190 | | | |
| gta | atg | tct | tac | gat | ttg | aga | gga | aat | tgg | gca | ggg | ttt | gct | gat | acc | 624 |
| Val | Met | Ser | Tyr | Asp | Leu | Arg | Gly | Asn | Trp | Ala | Gly | Phe | Ala | Asp | Thr | |
| | | 195 | | | | | 200 | | | | | 205 | | | | |
| cac | agt | ccc | ttg | tac | aga | agg | cca | cat | gat | caa | tat | gct | tat | gag | aaa | 672 |
| His | Ser | Pro | Leu | Tyr | Arg | Arg | Pro | His | Asp | Gln | Tyr | Ala | Tyr | Glu | Lys | |
| | 210 | | | | | 215 | | | | | 220 | | | | | |
| ctc | aat | gtg | aat | gat | gga | tta | caa | tta | tgg | gtt | gat | atg | ggt | tgt | cca | 720 |
| Leu | Asn | Val | Asn | Asp | Gly | Leu | Gln | Leu | Trp | Val | Asp | Met | Gly | Cys | Pro | |
| 225 | | | | | 230 | | | | | 235 | | | | | 240 | |
| gca | aac | aag | ttg | gtc | gtt | ggt | gtt | cca | ttt | tat | gga | aga | tcc | ttc | aca | 768 |
| Ala | Asn | Lys | Leu | Val | Val | Gly | Val | Pro | Phe | Tyr | Gly | Arg | Ser | Phe | Thr | |

```
                     245                 250                 255
ttg agc aac agc aat aag gac tac agg ttg gga acc tac atc aac aaa       816
Leu Ser Asn Ser Asn Lys Asp Tyr Arg Leu Gly Thr Tyr Ile Asn Lys
        260                 265                 270 gaa gct gga gga ggt gaa cct gga cct tac act aac gct acc gga ttt       864
Glu Ala Gly Gly Gly Glu Pro Gly Pro Tyr Thr Asn Ala Thr Gly Phe
            275                 280                 285 att tct tat tat gag ata tgc tta gaa gtt gat gat cct tcc aaa ggc       912
Ile Ser Tyr Tyr Glu Ile Cys Leu Glu Val Asp Asp Pro Ser Lys Gly
        290                 295                 300 tgg act aaa aaa tgg gac gaa cat gga aaa gtg cca tat gct tat aaa       960
Trp Thr Lys Lys Trp Asp Glu His Gly Lys Val Pro Tyr Ala Tyr Lys
305                 310                 315                 320 gga aat caa tgg gtt ggc tac gaa gac cca aaa tcc gtg gct ctg aag      1008
Gly Asn Gln Trp Val Gly Tyr Glu Asp Pro Lys Ser Val Ala Leu Lys
                325                 330                 335 atg gaa ttt att aaa tct aag ggt tat gga ggt gcc atg act tgg gcc      1056
Met Glu Phe Ile Lys Ser Lys Gly Tyr Gly Gly Ala Met Thr Trp Ala
            340                 345                 350 atc gac atg gac gat ttc caa gga gta tgc tct gat gac aaa cac acc      1104
Ile Asp Met Asp Asp Phe Gln Gly Val Cys Ser Asp Asp Lys His Thr
        355                 360                 365 ttg gcg gtc atc atg cac gat tac atg aag aat tat att gtt cct gaa      1152
Leu Ala Val Ile Met His Asp Tyr Met Lys Asn Tyr Ile Val Pro Glu
    370                 375                 380 ttt gat tcg agt cgg att act ccc agg cct gaa tgg gca aaa cca cca      1200
Phe Asp Ser Ser Arg Ile Thr Pro Arg Pro Glu Trp Ala Lys Pro Pro
385                 390                 395                 400 agc act cct tca caa gaa cca gac gac aca cca tac att ccc aca acc      1248
Ser Thr Pro Ser Gln Glu Pro Asp Asp Thr Pro Tyr Ile Pro Thr Thr
                405                 410                 415 cac gca cca aaa ccg agc cgc aaa cca acc aga aaa ccg aaa cca aca      1296
His Ala Pro Lys Pro Ser Arg Lys Pro Thr Arg Lys Pro Lys Pro Thr
            420                 425                 430 acc aca act gtg gcg gca acc act cct gtt gcc aca acg act aca gaa      1344
Thr Thr Thr Val Ala Ala Thr Thr Pro Val Ala Thr Thr Thr Thr Glu
        435                 440                 445 cac cat cac cac cat cac gaa gaa gag aag ccg agc gaa cag gac aac      1392
His His His His His His Glu Glu Glu Lys Pro Ser Glu Gln Asp Asn
    450                 455                 460 caa gtt ggt agc caa gat act act gca act gat gta gat tgt tcg cag      1440
Gln Val Gly Ser Gln Asp Thr Thr Ala Thr Asp Val Asp Cys Ser Gln
465                 470                 475                 480 gaa gac tat ttg cct cat gag gat tgc aac aag tat tac cgt tgt gtc      1488
Glu Asp Tyr Leu Pro His Glu Asp Cys Asn Lys Tyr Tyr Arg Cys Val
                485                 490                 495 cac gga gaa gca gtt ctc ttc act tgt cga gaa gga acc gtt tac cac      1536
His Gly Glu Ala Val Leu Phe Thr Cys Arg Glu Gly Thr Val Tyr His
            500                 505                 510 acc ata agc cac gtt tgt gat tgg gca tcg aat tca gac aga gaa aga      1584
Thr Ile Ser His Val Cys Asp Trp Ala Ser Asn Ser Asp Arg Glu Arg
        515                 520                 525 tgt cga gac tta aaa agc gtt cca cct cca aaa tta ttg act gat gaa      1632
Cys Arg Asp Leu Lys Ser Val Pro Pro Pro Lys Leu Leu Thr Asp Glu
    530                 535                 540 gaa ata gct aat aaa cta tcg aaa tat att gac tta cct ata ttg          1677
Glu Ile Ala Asn Lys Leu Ser Lys Tyr Ile Asp Leu Pro Ile Leu
545                 550                 555
```

<210> SEQ ID NO 14
<211> LENGTH: 559
<212> TYPE: PRT
<213> ORGANISM: Ctenocephalides felis

<400> SEQUENCE: 14

```
Asp Gln Lys Ala Arg Ile Val Cys Tyr Phe Ser Asn Trp Ala Val Tyr
 1               5                  10                  15

Arg Pro Gly Ile Gly Arg Tyr Gly Ile Glu Asp Ile Pro Val Asp Leu
             20                  25                  30

Cys Thr His Ile Val Tyr Ser Phe Ile Gly Val Asp Asp Lys Asp Trp
         35                  40                  45

Ser Val Leu Val Ile Asp Pro Glu Leu Asp Ile Asp Asp Asn Gly Phe
     50                  55                  60

Lys Asn Phe Thr Asn Leu Arg Lys Ile His Pro Asn Val Lys Leu Gln
 65                  70                  75                  80

Ile Ala Val Gly Gly Trp Ala Glu Gly Lys Lys Tyr Ser Thr Met
                 85                  90                  95

Val Ala Glu Lys Arg Lys Arg Ser Ala Phe Ile Arg Ser Val Val Asp
            100                 105                 110

Phe Met Asn Glu Tyr Lys Phe Asp Gly Phe Asp Leu Asp Trp Glu Tyr
        115                 120                 125

Pro Gly Ala Ala Asp Arg Gly Gly Ser Phe Ser Asp Lys Asp Lys Phe
    130                 135                 140

Leu Tyr Phe Val Gln Glu Leu Arg Arg Ala Phe Asn Lys Gln Gly Lys
145                 150                 155                 160

Asn Trp Glu Ile Thr Met Ala Val Pro Ile Ala Lys Phe Arg Leu Gln
                165                 170                 175

Glu Gly Tyr His Val Pro Glu Leu Cys Glu Leu Leu Asp Ala Ile His
            180                 185                 190

Val Met Ser Tyr Asp Leu Arg Gly Asn Trp Ala Gly Phe Ala Asp Thr
        195                 200                 205

His Ser Pro Leu Tyr Arg Arg Pro His Asp Gln Tyr Ala Tyr Glu Lys
    210                 215                 220

Leu Asn Val Asn Asp Gly Leu Gln Leu Trp Val Asp Met Gly Cys Pro
225                 230                 235                 240

Ala Asn Lys Leu Val Val Gly Val Pro Phe Tyr Gly Arg Ser Phe Thr
                245                 250                 255

Leu Ser Asn Ser Asn Lys Asp Tyr Arg Leu Gly Thr Tyr Ile Asn Lys
            260                 265                 270

Glu Ala Gly Gly Gly Glu Pro Gly Pro Tyr Thr Asn Ala Thr Gly Phe
        275                 280                 285

Ile Ser Tyr Tyr Glu Ile Cys Leu Glu Val Asp Asp Pro Ser Lys Gly
    290                 295                 300

Trp Thr Lys Lys Trp Asp Glu His Gly Lys Val Pro Tyr Ala Tyr Lys
305                 310                 315                 320

Gly Asn Gln Trp Val Gly Tyr Glu Asp Pro Lys Ser Val Ala Leu Lys
                325                 330                 335

Met Glu Phe Ile Lys Ser Lys Gly Tyr Gly Gly Ala Met Thr Trp Ala
            340                 345                 350

Ile Asp Met Asp Asp Phe Gln Gly Val Cys Ser Asp Lys His Thr
        355                 360                 365

Leu Ala Val Ile Met His Asp Tyr Met Lys Asn Tyr Ile Val Pro Glu
    370                 375                 380
```

```
Phe Asp Ser Ser Arg Ile Thr Pro Arg Pro Glu Trp Ala Lys Pro Pro
385                 390                 395                 400

Ser Thr Pro Ser Gln Glu Pro Asp Asp Thr Pro Tyr Ile Pro Thr Thr
            405                 410                 415

His Ala Pro Lys Pro Ser Arg Lys Pro Thr Arg Lys Pro Lys Pro Thr
            420                 425                 430

Thr Thr Thr Val Ala Ala Thr Thr Pro Val Ala Thr Thr Thr Thr Glu
            435                 440                 445

His His His His His His Glu Glu Lys Pro Ser Glu Gln Asp Asn
            450                 455                 460

Gln Val Gly Ser Gln Asp Thr Thr Ala Thr Asp Val Asp Cys Ser Gln
465                 470                 475                 480

Glu Asp Tyr Leu Pro His Glu Asp Cys Asn Lys Tyr Tyr Arg Cys Val
                485                 490                 495

His Gly Glu Ala Val Leu Phe Thr Cys Arg Glu Gly Thr Val Tyr His
            500                 505                 510

Thr Ile Ser His Val Cys Asp Trp Ala Ser Asn Ser Asp Arg Glu Arg
            515                 520                 525

Cys Arg Asp Leu Lys Ser Val Pro Pro Lys Leu Leu Thr Asp Glu
            530                 535                 540

Glu Ile Ala Asn Lys Leu Ser Lys Tyr Ile Asp Leu Pro Ile Leu
545                 550                 555
```

<210> SEQ ID NO 15
<211> LENGTH: 1677
<212> TYPE: DNA
<213> ORGANISM: Ctenocephalides felis

<400> SEQUENCE: 15

```
caatataggt aagtcaatat atttcgatag tttattagct atttcttcat cagtcaataa      60
ttttggaggt ggaacgcttt ttaagtctcg acatctttct ctgtctgaat tcgatgccca    120
atcacaaacg tggcttatgg tgtggtaaac ggttccttct cgacaagtga agagaactgc    180
ttctccgtgg acacaacggt aatacttgtt gcaatcctca tgaggcaaat agtcttcctg    240
cgaacaatct acatcagttg cagtagtatc ttggctacca acttggttgt cctgttcgct    300
cggcttctct tcttcgtgat ggtggtgatg gtgttctgta gtcgttgtgg caacaggagt    360
ggttgccgcc acagtgtgg ttgttggttt cggttttctg gttggtttgc ggctcggttt    420
tggtgcgtgg gttgtgggaa tgtatggtgt gtcgtctggt tcttgtgaag gagtgcttgg    480
tggttttgcc cattcaggcc tgggagtaat ccgactcgaa tcaaattcag gaacaatata    540
attcttcatg taatcgtgca tgatgaccgc caaggtgtgt tgtcatcag agcatactcc    600
ttggaaatcg tccatgtcga tggcccaagt catggcacct ccataaccct tagatttaat    660
aaattccatc ttcagagcca cggattttgg gtcttcgtag ccaacccatt gatttccttt    720
ataagcatat ggcactttc catgttcgtc ccattttta gtccagcctt tggaaggatc    780
atcaacttct aagcatatct cataataaga aataaatccg gtagcgttag tgtaaggtcc    840
aggttcacct cctccagctt ctttgttgat gtaggttccc aacctgtagt ccttattgct    900
gttgctcaat gtgaaggatc ttccataaaa tggaacacca cgaccaact tgtttgctgg    960
acaacccata tcaacccata attgtaatcc atcattcaca ttgagtttct cataagcata   1020
ttgatcatgt ggccttctgt acaagggact gtgggtatca gcaaaccctg cccaatttcc   1080
tctcaaatcg taagacatta cgtggatagc atctaataat tcgcaaagtt ctggtacatg   1140
```

-continued

```
atatccttcc tgcagcctaa atttggcaat cgggacagcc atggtgatct cccagttttt    1200
gccttgtttg ttgaaagccc ttcgcaattc ttggacaaag tataaaaatt tgtctttgtc    1260
ggaaaaactg ccacctctat cagcagcacc aggatactcc caatccaagt cgaaaccgtc    1320
gaacttgtat tcgttcatga aatcaactac actgcgaata aaggctgatc tcttcctctt    1380
ttcggccacc atggtcgaat attttttccc gccttcagcc catcctccga cggctatttg    1440
taatttcaca tttggatgaa tttttctcaa atttgtgaaa ttcttgaaac cattgtcatc    1500
tatgtccaac tctgggtcga tgaccagcac gctccagtct tgtcgtcta ctccgatgaa    1560 agaataaact atatgggtac acaagtcaac tggtatgtcc tctatgccat atctgcctat    1620
tccgggcctg taaactgccc aattgctgaa gtaacatact atcctggcct tctggtc       1677
```

<210> SEQ ID NO 16
<211> LENGTH: 115
<212> TYPE: DNA
<213> ORGANISM: Ctenocephalides felis
<220> FEATURE:
<221> NAME/KEY: CDS
<222> LOCATION: (2)..(115)

<400> SEQUENCE: 16

```
t gaa ggc gga aaa aaa tat tcg acc atg gtg gcc gaa aag agg aag aga     49
  Glu Gly Gly Lys Lys Tyr Ser Thr Met Val Ala Glu Lys Arg Lys Arg
    1               5                  10                  15 tca gcc ttt att cgc agt gta gtt gat ttc atg aac gaa tac aag ttc     97
Ser Ala Phe Ile Arg Ser Val Val Asp Phe Met Asn Glu Tyr Lys Phe
            20                  25                  30 gac ggt ttc gac ttg gat                                            115
Asp Gly Phe Asp Leu Asp
        35
```

<210> SEQ ID NO 17
<211> LENGTH: 38
<212> TYPE: PRT
<213> ORGANISM: Ctenocephalides felis

<400> SEQUENCE: 17

```
Glu Gly Gly Lys Lys Tyr Ser Thr Met Val Ala Glu Lys Arg Lys Arg
  1               5                  10                  15

Ser Ala Phe Ile Arg Ser Val Val Asp Phe Met Asn Glu Tyr Lys Phe
            20                  25                  30

Asp Gly Phe Asp Leu Asp
        35
```

<210> SEQ ID NO 18
<211> LENGTH: 115
<212> TYPE: DNA
<213> ORGANISM: Ctenocephalides felis

<400> SEQUENCE: 18

```
atccaagtcg aaaccgtcga acttgtattc gttcatgaaa tcaactacac tgcgaataaa     60
ggctgatctc ttcctctttt cggccaccat ggtcgaatat ttttttccgc cttca         115
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gcwgcnccng grtaytccca                                           20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 20
atgrtngcwg twggwggwtg ggc                                       23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 21
agcaaaccct gcccaatttc c                                         21

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
ccatcctaat acgactcact atagggc                                   27

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23
tttttccgcc ttcagcccat c                                         21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 24
actcactata gggctcgagc ggc                                       23

<210> SEQ ID NO 25
<211> LENGTH: 276
<212> TYPE: DNA
<213> ORGANISM: Ctenocephalides felis
<220> FEATURE:
<221> NAME/KEY: CDS
<222> LOCATION: (1)..(276)

<400> SEQUENCE: 25

-continued

```
gac cag aag gcc agg ata gta tgt tac ttc agc aat tgg gca gtt tac      48
Asp Gln Lys Ala Arg Ile Val Cys Tyr Phe Ser Asn Trp Ala Val Tyr
 1               5                  10                  15 agg ccc gga ata ggc aga tat ggc ata gaa gac ata cca gtt gac ttg      96
Arg Pro Gly Ile Gly Arg Tyr Gly Ile Glu Asp Ile Pro Val Asp Leu
            20                  25                  30 tgt acc cat ata gtt tat tct ttc atc gga gta gac gac aaa gac tgg     144
Cys Thr His Ile Val Tyr Ser Phe Ile Gly Val Asp Asp Lys Asp Trp
         35                  40                  45 agc gtg ctg gtc atc gac ccg gag ttg gac ata gat gac aat ggt ttt     192
Ser Val Leu Val Ile Asp Pro Glu Leu Asp Ile Asp Asp Asn Gly Phe
 50                  55                  60 aag aat ttc aca aac ttg aga aaa gcc cat cca aat gtt aaa tta caa     240
Lys Asn Phe Thr Asn Leu Arg Lys Ala His Pro Asn Val Lys Leu Gln
 65                  70                  75                  80 ata gcc gtc gga gga tgg gct gaa ggc gga aaa aaa                     276
Ile Ala Val Gly Gly Trp Ala Glu Gly Gly Lys Lys
                 85                  90
```

<210> SEQ ID NO 26
<211> LENGTH: 92
<212> TYPE: PRT
<213> ORGANISM: Ctenocephalides felis

<400> SEQUENCE: 26

```
Asp Gln Lys Ala Arg Ile Val Cys Tyr Phe Ser Asn Trp Ala Val Tyr
 1               5                  10                  15

Arg Pro Gly Ile Gly Arg Tyr Gly Ile Glu Asp Ile Pro Val Asp Leu
            20                  25                  30

Cys Thr His Ile Val Tyr Ser Phe Ile Gly Val Asp Asp Lys Asp Trp
         35                  40                  45

Ser Val Leu Val Ile Asp Pro Glu Leu Asp Ile Asp Asp Asn Gly Phe
 50                  55                  60

Lys Asn Phe Thr Asn Leu Arg Lys Ala His Pro Asn Val Lys Leu Gln
 65                  70                  75                  80

Ile Ala Val Gly Gly Trp Ala Glu Gly Gly Lys Lys
                 85                  90
```

<210> SEQ ID NO 27
<211> LENGTH: 276
<212> TYPE: DNA
<213> ORGANISM: Ctenocephalides felis

<400> SEQUENCE: 27

```
gaccagaagg ccaggatagt atgttacttc agcaattggg cagtttacag gcccggaata      60
ggcagatatg gcatagaaga cataccagtt gacttgtgta cccatatagt ttattctttc     120
atcggagtag acgacaaaga ctggagcgtg ctggtcatcg acccggagtt ggacatagat     180
gacaatggtt ttaagaattt cacaaacttg agaaaagccc atccaaatgt aaattacaa      240
atagccgtcg gaggatgggc tgaaggcgga aaaaaa                              276
```

<210> SEQ ID NO 28
<211> LENGTH: 1478
<212> TYPE: DNA
<213> ORGANISM: Tagged Ctenocephalides felis
<220> FEATURE:
<221> NAME/KEY: CDS
<222> LOCATION: (1)..(1467)

<400> SEQUENCE: 28

```
atg cgg ggt tct cat cat cat cat cat cat ggt atg gct agc atg act      48
Met Arg Gly Ser His His His His His His Gly Met Ala Ser Met Thr
 1               5                  10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 ccg gtg aaa tta caa ata gcc gtc gga gga tgg gct gaa ggc gga aaa     144
Pro Val Lys Leu Gln Ile Ala Val Gly Gly Trp Ala Glu Gly Gly Lys
        35                  40                  45 aaa tat tcg acc atg gtg gcc gaa aag agg aag aga tca gcc ttt att     192
Lys Tyr Ser Thr Met Val Ala Glu Lys Arg Lys Arg Ser Ala Phe Ile
    50                  55                  60 cgc agt gta gtt gat ttc atg aac gaa tac aag ttc gac ggt ttc gac     240
Arg Ser Val Val Asp Phe Met Asn Glu Tyr Lys Phe Asp Gly Phe Asp
65                  70                  75                  80 ttg gat tgg gag tat cct ggt gct gct gat aga ggt ggc agt ttt tcc     288
Leu Asp Trp Glu Tyr Pro Gly Ala Ala Asp Arg Gly Gly Ser Phe Ser
                85                  90                  95 gac aaa gac aaa ttt tta tac ttt gtc caa gaa ttg cga agg gct ttc     336
Asp Lys Asp Lys Phe Leu Tyr Phe Val Gln Glu Leu Arg Arg Ala Phe
            100                 105                 110 aac aaa caa ggc aaa aac tgg gag atc acc atg gct gtc ccg att gcc     384
Asn Lys Gln Gly Lys Asn Trp Glu Ile Thr Met Ala Val Pro Ile Ala
        115                 120                 125 aaa ttt agg ctg cag gaa gga tat cat gta cca gaa ctt tgc gaa tta     432
Lys Phe Arg Leu Gln Glu Gly Tyr His Val Pro Glu Leu Cys Glu Leu
    130                 135                 140 tta gat gct atc cac gta atg tct tac gat ttg aga gga aat tgg gca     480
Leu Asp Ala Ile His Val Met Ser Tyr Asp Leu Arg Gly Asn Trp Ala
145                 150                 155                 160 ggg ttt gct gat acc cac agt ccc ttg tac aga agg cca cat gat caa     528
Gly Phe Ala Asp Thr His Ser Pro Leu Tyr Arg Arg Pro His Asp Gln
                165                 170                 175 tat gct tat gag aaa ctc aat gtg aat gat gga tta caa tta tgg gtt     576
Tyr Ala Tyr Glu Lys Leu Asn Val Asn Asp Gly Leu Gln Leu Trp Val
            180                 185                 190 gat atg ggt tgt cca gca aac aag ttg gtc gtt ggt gtt cca ttt tat     624
Asp Met Gly Cys Pro Ala Asn Lys Leu Val Val Gly Val Pro Phe Tyr
        195                 200                 205 gga aga tcc ttc aca ttg agc aac agc aat aag gac tac agg ttg gga     672
Gly Arg Ser Phe Thr Leu Ser Asn Ser Asn Lys Asp Tyr Arg Leu Gly
    210                 215                 220 acc tac atc aac aaa gaa gct gga gga ggt gaa cct gga cct tac act     720
Thr Tyr Ile Asn Lys Glu Ala Gly Gly Gly Glu Pro Gly Pro Tyr Thr
225                 230                 235                 240 aac gct acc gga ttt att tct tat tat gag ata tgc tta gaa gtt gat     768
Asn Ala Thr Gly Phe Ile Ser Tyr Tyr Glu Ile Cys Leu Glu Val Asp
                245                 250                 255 gat cct tcc aaa ggc tgg act aaa aaa tgg gac gaa cat gga aaa gtg     816
Asp Pro Ser Lys Gly Trp Thr Lys Lys Trp Asp Glu His Gly Lys Val
            260                 265                 270 cca tat gct tat aaa gga aat caa tgg gtt ggc tac gaa gac cca aaa     864
Pro Tyr Ala Tyr Lys Gly Asn Gln Trp Val Gly Tyr Glu Asp Pro Lys
        275                 280                 285 tcc gtg gct ctg aag atg gaa ttt att aaa tct aag ggt tat gga ggt     912
Ser Val Ala Leu Lys Met Glu Phe Ile Lys Ser Lys Gly Tyr Gly Gly
    290                 295                 300 gcc atg act tgg gcc atc gac atg gac gat ttc caa gga gta tgc tct     960
Ala Met Thr Trp Ala Ile Asp Met Asp Asp Phe Gln Gly Val Cys Ser
```

```
                305                  310                  315                  320
gat gac aaa cac acc ttg gcg gtc atc atg cac gat tac atg aag aat            1008
Asp Asp Lys His Thr Leu Ala Val Ile Met His Asp Tyr Met Lys Asn
                    325                  330                  335 tat att gtt cct gaa ttt gat tcg agt cgg att act ccc agg cct gaa            1056
Tyr Ile Val Pro Glu Phe Asp Ser Ser Arg Ile Thr Pro Arg Pro Glu
                    340                  345                  350 tgg gca aaa cca cca agc act cct tca caa gaa cca gac gac aca cca            1104
Trp Ala Lys Pro Pro Ser Thr Pro Ser Gln Glu Pro Asp Asp Thr Pro
                    355                  360                  365 tac att ccc aca acc cac gca cca aaa ccg agc cgc aaa cca acc aga            1152
Tyr Ile Pro Thr Thr His Ala Pro Lys Pro Ser Arg Lys Pro Thr Arg
        370                  375                  380 aaa ccg aaa cca aca acc aca act gtg gcg gca acc act cct gtt gcc            1200
Lys Pro Lys Pro Thr Thr Thr Thr Val Ala Ala Thr Thr Pro Val Ala
385                  390                  395                  400 aca acg act aca gaa cac cat cac cac cat cac gaa gaa gag aag ccg            1248
Thr Thr Thr Thr Glu His His His His His His Glu Glu Glu Lys Pro
                    405                  410                  415 agc gaa cag gac aac caa gtt ggt agc caa gat act act gca act gat            1296
Ser Glu Gln Asp Asn Gln Val Gly Ser Gln Asp Thr Thr Ala Thr Asp
                420                  425                  430 gta gat tgt tcg cag gaa gac tat ttg cct cat gag gat tgc aac aag            1344
Val Asp Cys Ser Gln Glu Asp Tyr Leu Pro His Glu Asp Cys Asn Lys
            435                  440                  445 tat tac cgt tgt gtc cac gga gaa gca gtt ctc ttc act tgt cga gaa            1392
Tyr Tyr Arg Cys Val His Gly Glu Ala Val Leu Phe Thr Cys Arg Glu
        450                  455                  460 gga acc gtt tac cac acc ata agc cac gtt tgt gat tgg gca tcg aat            1440
Gly Thr Val Tyr His Thr Ile Ser His Val Cys Asp Trp Ala Ser Asn
465                  470                  475                  480 tca gac aga gaa aga tgt cga gac tta taactcgaga a                           1478
Ser Asp Arg Glu Arg Cys Arg Asp Leu
                485
```

<210> SEQ ID NO 29
<211> LENGTH: 489
<212> TYPE: PRT
<213> ORGANISM: Tagged Ctenocephalides felis

<400> SEQUENCE: 29

```
Met Arg Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Pro Val Lys Leu Gln Ile Ala Val Gly Gly Trp Ala Glu Gly Gly Lys
            35                  40                  45

Lys Tyr Ser Thr Met Val Ala Glu Lys Arg Lys Arg Ser Ala Phe Ile
        50                  55                  60

Arg Ser Val Val Asp Phe Met Asn Glu Tyr Lys Phe Asp Gly Phe Asp
65                  70                  75                  80

Leu Asp Trp Glu Tyr Pro Gly Ala Ala Asp Arg Gly Gly Ser Phe Ser
                85                  90                  95

Asp Lys Asp Lys Phe Leu Tyr Phe Val Gln Glu Leu Arg Arg Ala Phe
            100                 105                 110

Asn Lys Gln Gly Lys Asn Trp Glu Ile Thr Met Ala Val Pro Ile Ala
        115                 120                 125

Lys Phe Arg Leu Gln Glu Gly Tyr His Val Pro Glu Leu Cys Glu Leu
```

```
            130                 135                 140
Leu Asp Ala Ile His Val Met Ser Tyr Asp Leu Arg Gly Asn Trp Ala
145                 150                 155                 160
Gly Phe Ala Asp Thr His Ser Pro Leu Tyr Arg Arg Pro His Asp Gln
                165                 170                 175
Tyr Ala Tyr Glu Lys Leu Asn Val Asn Asp Gly Leu Gln Leu Trp Val
            180                 185                 190
Asp Met Gly Cys Pro Ala Asn Lys Leu Val Val Gly Val Pro Phe Tyr
            195                 200                 205
Gly Arg Ser Phe Thr Leu Ser Asn Ser Asn Lys Asp Tyr Arg Leu Gly
            210                 215                 220
Thr Tyr Ile Asn Lys Glu Ala Gly Gly Gly Glu Pro Gly Pro Tyr Thr
225                 230                 235                 240
Asn Ala Thr Gly Phe Ile Ser Tyr Tyr Glu Ile Cys Leu Glu Val Asp
                245                 250                 255
Asp Pro Ser Lys Gly Trp Thr Lys Lys Trp Asp Glu His Gly Lys Val
                260                 265                 270
Pro Tyr Ala Tyr Lys Gly Asn Gln Trp Val Gly Tyr Glu Asp Pro Lys
            275                 280                 285
Ser Val Ala Leu Lys Met Glu Phe Ile Lys Ser Lys Gly Tyr Gly Gly
            290                 295                 300
Ala Met Thr Trp Ala Ile Asp Met Asp Asp Phe Gln Gly Val Cys Ser
305                 310                 315                 320
Asp Asp Lys His Thr Leu Ala Val Ile Met His Asp Tyr Met Lys Asn
                325                 330                 335
Tyr Ile Val Pro Glu Phe Asp Ser Ser Arg Ile Thr Pro Arg Pro Glu
                340                 345                 350
Trp Ala Lys Pro Pro Ser Thr Pro Ser Gln Glu Pro Asp Asp Thr Pro
                355                 360                 365
Tyr Ile Pro Thr Thr His Ala Pro Lys Pro Ser Arg Lys Pro Thr Arg
            370                 375                 380
Lys Pro Lys Pro Thr Thr Thr Thr Val Ala Ala Thr Thr Pro Val Ala
385                 390                 395                 400
Thr Thr Thr Thr Glu His His His His His Glu Glu Lys Pro
                405                 410                 415
Ser Glu Gln Asp Asn Gln Val Gly Ser Gln Asp Thr Thr Ala Thr Asp
            420                 425                 430
Val Asp Cys Ser Gln Glu Asp Tyr Leu Pro His Glu Asp Cys Asn Lys
            435                 440                 445
Tyr Tyr Arg Cys Val His Gly Glu Ala Val Leu Phe Thr Cys Arg Glu
        450                 455                 460
Gly Thr Val Tyr His Thr Ile Ser His Val Cys Asp Trp Ala Ser Asn
465                 470                 475                 480
Ser Asp Arg Glu Arg Cys Arg Asp Leu
                485

<210> SEQ ID NO 30
<211> LENGTH: 1478
<212> TYPE: DNA
<213> ORGANISM: Tagged Ctenocephalides felis

<400> SEQUENCE: 30
ttctcgagtt ataagtctcg acatctttct ctgtctgaat tcgatgccca atcacaaacg      60
tggcttatgg tgtggtaaac ggttccttct cgacaagtga agagaactgc ttctccgtgg    120
```

-continued

```
acacaacggt aatacttgtt gcaatcctca tgaggcaaat agtcttcctg cgaacaatct    180
acatcagttg cagtagtatc ttggctacca acttggttgt cctgttcgct cggcttctct    240
tcttcgtgat ggtggtgatg gtgttctgta gtcgttgtgg caacaggagt ggttgccgcc    300
acagttgtgg ttgttggttt cggttttctg gttggtttgc ggctcggttt tggtgcgtgg    360
gttgtgggaa tgtatggtgt gtcgtctggt tcttgtgaag gagtgcttgg tggttttgcc    420
cattcaggcc tgggagtaat ccgactcgaa tcaaattcag gaacaatata attcttcatg    480
taatcgtgca tgatgaccgc caaggtgtgt tgtcatcag agcatactcc ttggaaatcg     540
tccatgtcga tggcccaagt catggcacct ccataaccct tagatttaat aaattccatc    600
ttcagagcca cggattttgg gtcttcgtag ccaacccatt gatttccttt ataagcatat    660
ggcacttttc catgttcgtc ccatttttta gtccagcctt tggaaggatc atcaacttct    720
aagcatatct cataataaga aataaatccg gtagcgttag tgtaaggtcc aggttcacct    780
cctccagctt ctttgttgat gtaggttccc aacctgtagt ccttattgct gttgctcaat    840
gtgaaggatc ttccataaaa tggaacacca acgaccaact tgtttgctgg acaacccata    900
tcaacccata attgtaatcc atcattcaca ttgagtttct cataagcata ttgatcatgt    960
ggccttctgt acaagggact gtgggtatca gcaaaccctg cccaatttcc tctcaaatcg   1020
taagacatta cgtggatagc atctaataat tcgcaaagtt ctggtacatg atatccttcc   1080
tgcagcctaa atttggcaat cgggacagcc atggtgatct cccagttttt gccttgtttg   1140
ttgaaagccc ttcgcaattc ttggacaaag tataaaaatt tgtctttgtc ggaaaaactg   1200
ccacctctat cagcagcacc aggatactcc caatccaagt cgaaaccgtc gaacttgtat   1260
tcgttcatga aatcaactac actgcgaata aaggctgatc tcttcctctt tcggccacc    1320
atggtcgaat attttttcc gccttcagcc catcctccga cggctatttg taatttcacc    1380
ggatccttat cgtcatcgtc gtacagatcc cgacccattt gctgtccacc agtcatgcta   1440
gccataccat gatgatgatg atgatgagaa ccccgcat                           1478
```

<210> SEQ ID NO 31
<211> LENGTH: 1919
<212> TYPE: DNA
<213> ORGANISM: Tagged Ctenocephalides felis
<220> FEATURE:
<221> NAME/KEY: CDS
<222> LOCATION: (12)..(1916)

<400> SEQUENCE: 31

```
ttaagcttga a atg gga aga cac tgg aac ttg tta gcc gtt ttg tgc gcc           50
            Met Gly Arg His Trp Asn Leu Leu Ala Val Leu Cys Ala
              1               5                  10 ata gca atc tct tca att aat aca gtt gaa gca tca gac cag aag gcc            98
Ile Ala Ile Ser Ser Ile Asn Thr Val Glu Ala Ser Asp Gln Lys Ala
 15              20                  25 agg ata gta tgt tac ttc agc aat tgg gca gtt tac agg ccc gga ata          146
Arg Ile Val Cys Tyr Phe Ser Asn Trp Ala Val Tyr Arg Pro Gly Ile
 30              35                  40                  45 ggc aga tat ggc ata gag gac ata cca gtt gac ttg tgt acc cat ata          194
Gly Arg Tyr Gly Ile Glu Asp Ile Pro Val Asp Leu Cys Thr His Ile
                 50                  55                  60 gtt tat tct ttc atc gga gta gac gac aaa gac tgg agc gtg ctg gtc          242
Val Tyr Ser Phe Ile Gly Val Asp Asp Lys Asp Trp Ser Val Leu Val
             65                  70                  75 atc gac cca gag ttg gac ata gat gac aat ggt ttc aag aat ttc aca          290
```

-continued

```
            Ile Asp Pro Glu Leu Asp Ile Asp Asp Asn Gly Phe Lys Asn Phe Thr
                    80                  85                  90 aat ttg aga aaa att cat cca aat gtg aaa tta caa ata gcc gtc gga            338
Asn Leu Arg Lys Ile His Pro Asn Val Lys Leu Gln Ile Ala Val Gly
     95                 100                 105 gga tgg gct gaa ggc gga aaa aaa tat tcg acc atg gtg gcc gaa aag            386
Gly Trp Ala Glu Gly Gly Lys Lys Tyr Ser Thr Met Val Ala Glu Lys
110                 115                 120                 125 agg aag aga tca gcc ttt att cgc agt gta gtt gat ttc atg aac gaa            434
Arg Lys Arg Ser Ala Phe Ile Arg Ser Val Val Asp Phe Met Asn Glu
                130                 135                 140 tac aag ttc gac ggt ttc gac ttg gat tgg gag tat cct ggt gct gct            482
Tyr Lys Phe Asp Gly Phe Asp Leu Asp Trp Glu Tyr Pro Gly Ala Ala
            145                 150                 155 gat aga ggt ggc agt ttt tcc gac aaa gac aaa ttt tta tac ttt gtc            530
Asp Arg Gly Gly Ser Phe Ser Asp Lys Asp Lys Phe Leu Tyr Phe Val
        160                 165                 170 caa gaa ttg cga agg gct ttc aac aaa caa ggc aaa aac tgg gag atc            578
Gln Glu Leu Arg Arg Ala Phe Asn Lys Gln Gly Lys Asn Trp Glu Ile
    175                 180                 185 acc atg gct gtc ccg att gcc aaa ttt agg ctg cag gaa gga tat cat            626
Thr Met Ala Val Pro Ile Ala Lys Phe Arg Leu Gln Glu Gly Tyr His
190                 195                 200                 205 gta cca gaa ctt tgc gaa tta tta gat gct atc cac gta atg tct tac            674
Val Pro Glu Leu Cys Glu Leu Leu Asp Ala Ile His Val Met Ser Tyr
                210                 215                 220 gat ttg aga gga aat tgg gca ggg ttt gct gat acc cac agt ccc ttg            722
Asp Leu Arg Gly Asn Trp Ala Gly Phe Ala Asp Thr His Ser Pro Leu
            225                 230                 235 tac aga agg cca cat gat caa tat gct tat gag aaa ctc aat gtg aat            770
Tyr Arg Arg Pro His Asp Gln Tyr Ala Tyr Glu Lys Leu Asn Val Asn
        240                 245                 250 gat gga tta caa tta tgg gtt gat atg ggt tgt cca gca aac aag ttg            818
Asp Gly Leu Gln Leu Trp Val Asp Met Gly Cys Pro Ala Asn Lys Leu
    255                 260                 265 gtc gtt ggt gtt cca ttt tat gga aga ttc ttc aca ttg agc aac agc            866
Val Val Gly Val Pro Phe Tyr Gly Arg Phe Phe Thr Leu Ser Asn Ser
270                 275                 280                 285 aat aag gac tac agg ttg gga acc tac atc aac aaa gaa gct gga gga            914
Asn Lys Asp Tyr Arg Leu Gly Thr Tyr Ile Asn Lys Glu Ala Gly Gly
                290                 295                 300 ggt gaa cct gga cct tac act aac gct acc gga ttt att tct tat tat            962
Gly Glu Pro Gly Pro Tyr Thr Asn Ala Thr Gly Phe Ile Ser Tyr Tyr
            305                 310                 315 gag ata tgc tta gaa gtt gat gat cct tcc aaa ggc tgg act aaa aaa           1010
Glu Ile Cys Leu Glu Val Asp Asp Pro Ser Lys Gly Trp Thr Lys Lys
        320                 325                 330 tgg gac gaa cat gga aaa gtg cca tat gct tat aaa gga aat caa tgg           1058
Trp Asp Glu His Gly Lys Val Pro Tyr Ala Tyr Lys Gly Asn Gln Trp
    335                 340                 345 gtt ggc tac gaa gac cca aaa tcc gtg gct ctg aag atg gaa ttt att           1106
Val Gly Tyr Glu Asp Pro Lys Ser Val Ala Leu Lys Met Glu Phe Ile
350                 355                 360                 365 aaa tct aag ggt tat gga ggt gcc atg act tgg gcc atc gac atg gac           1154
Lys Ser Lys Gly Tyr Gly Gly Ala Met Thr Trp Ala Ile Asp Met Asp
                370                 375                 380 gat ttc caa gga gta tgc tct gat gac aaa cac acc ttg gcg gtc atc           1202
Asp Phe Gln Gly Val Cys Ser Asp Asp Lys His Thr Leu Ala Val Ile
            385                 390                 395
```

-continued

```
atg cac gat tac atg aag aat tat att gtt cct gaa ttt gat tcg agt    1250
Met His Asp Tyr Met Lys Asn Tyr Ile Val Pro Glu Phe Asp Ser Ser
    400                 405                 410 cgg att act ccc agg cct gaa tgg gca aaa cca cca agc act cct tca    1298
Arg Ile Thr Pro Arg Pro Glu Trp Ala Lys Pro Pro Ser Thr Pro Ser
415                 420                 425 caa gaa cca gac gac aca cca tac att ccc aca acc cac gca cca aaa    1346
Gln Glu Pro Asp Asp Thr Pro Tyr Ile Pro Thr Thr His Ala Pro Lys
430                 435                 440                 445 ccg agc cgc aaa cca acc aga aaa ccg aaa cca aca acc aca act gtg    1394
Pro Ser Arg Lys Pro Thr Arg Lys Pro Lys Pro Thr Thr Thr Thr Val
                450                 455                 460 gcg gca acc act cct gtt gcc aca acg act aca gaa cac cat cac cac    1442
Ala Ala Thr Thr Pro Val Ala Thr Thr Thr Thr Glu His His His His
            465                 470                 475 cat cac gaa gaa gag aag ccg agc gaa cag gac aac caa gtt ggt agc    1490
His His Glu Glu Glu Lys Pro Ser Glu Gln Asp Asn Gln Val Gly Ser
        480                 485                 490 caa gat act act gca act gat gta gat tgt tcg cag gaa gac tat ttg    1538
Gln Asp Thr Thr Ala Thr Asp Val Asp Cys Ser Gln Glu Asp Tyr Leu
495                 500                 505 cct cat gag gat tgc aac aag tat tac cgt tgt gtc cac gga gaa gca    1586
Pro His Glu Asp Cys Asn Lys Tyr Tyr Arg Cys Val His Gly Glu Ala
510                 515                 520                 525 gtt ctc ttc act tgt cga gaa gga acc gtt tac cac acc ata agc cac    1634
Val Leu Phe Thr Cys Arg Glu Gly Thr Val Tyr His Thr Ile Ser His
                530                 535                 540 gtt tgt gat tgg gca tcg aat tca gac aga gaa aga tgt cga gac tta    1682
Val Cys Asp Trp Ala Ser Asn Ser Asp Arg Glu Arg Cys Arg Asp Leu
            545                 550                 555 aaa agc gtt cca cct cca aaa tta ttg act gat gaa gaa ata gct aat    1730
Lys Ser Val Pro Pro Pro Lys Leu Leu Thr Asp Glu Glu Ile Ala Asn
        560                 565                 570 aaa cta tcg aaa tat att gac tta cct ata ttg gga tcc act agt cca    1778
Lys Leu Ser Lys Tyr Ile Asp Leu Pro Ile Leu Gly Ser Thr Ser Pro
575                 580                 585 gtg tgg tgg aat tct gca gat atc cag cac agt ggc ggc cgc tcg agt    1826
Val Trp Trp Asn Ser Ala Asp Ile Gln His Ser Gly Gly Arg Ser Ser
590                 595                 600                 605 cta gag ggc ccg cgg ttc gaa ggt aag cct atc cct aac cct ctc ctc    1874
Leu Glu Gly Pro Arg Phe Glu Gly Lys Pro Ile Pro Asn Pro Leu Leu
                610                 615                 620 ggt ctc gat tct acg cgt acc ggt cat cat cac cat cac cat tga        1919
Gly Leu Asp Ser Thr Arg Thr Gly His His His His His His
            625                 630                 635
```

<210> SEQ ID NO 32
<211> LENGTH: 635
<212> TYPE: PRT
<213> ORGANISM: Tagged Ctenocephalides felis

<400> SEQUENCE: 32

```
Met Gly Arg His Trp Asn Leu Leu Ala Val Leu Cys Ala Ile Ala Ile
 1               5                  10                  15

Ser Ser Ile Asn Thr Val Glu Ala Ser Asp Gln Lys Ala Arg Ile Val
            20                  25                  30

Cys Tyr Phe Ser Asn Trp Ala Val Tyr Arg Pro Gly Ile Gly Arg Tyr
        35                  40                  45

Gly Ile Glu Asp Ile Pro Val Asp Leu Cys Thr His Ile Val Tyr Ser
    50                  55                  60
```

```
Phe Ile Gly Val Asp Asp Lys Asp Trp Ser Val Leu Val Ile Asp Pro
 65                  70                  75                  80

Glu Leu Asp Ile Asp Asp Asn Gly Phe Lys Asn Phe Thr Asn Leu Arg
                 85                  90                  95

Lys Ile His Pro Asn Val Lys Leu Gln Ile Ala Val Gly Gly Trp Ala
            100                 105                 110

Glu Gly Gly Lys Lys Tyr Ser Thr Met Val Ala Glu Lys Arg Lys Arg
        115                 120                 125

Ser Ala Phe Ile Arg Ser Val Val Asp Phe Met Asn Glu Tyr Lys Phe
130                 135                 140

Asp Gly Phe Asp Leu Asp Trp Glu Tyr Pro Gly Ala Ala Asp Arg Gly
145                 150                 155                 160

Gly Ser Phe Ser Asp Lys Asp Lys Phe Leu Tyr Phe Val Gln Glu Leu
                165                 170                 175

Arg Arg Ala Phe Asn Lys Gln Gly Lys Asn Trp Glu Ile Thr Met Ala
            180                 185                 190

Val Pro Ile Ala Lys Phe Arg Leu Gln Glu Gly Tyr His Val Pro Glu
        195                 200                 205

Leu Cys Glu Leu Leu Asp Ala Ile His Val Met Ser Tyr Asp Leu Arg
210                 215                 220

Gly Asn Trp Ala Gly Phe Ala Asp Thr His Ser Pro Leu Tyr Arg Arg
225                 230                 235                 240

Pro His Asp Gln Tyr Ala Tyr Glu Lys Leu Asn Val Asn Asp Gly Leu
                245                 250                 255

Gln Leu Trp Val Asp Met Gly Cys Pro Ala Asn Lys Leu Val Val Gly
            260                 265                 270

Val Pro Phe Tyr Gly Arg Phe Phe Thr Leu Ser Asn Ser Asn Lys Asp
        275                 280                 285

Tyr Arg Leu Gly Thr Tyr Ile Asn Lys Glu Ala Gly Gly Gly Glu Pro
290                 295                 300

Gly Pro Tyr Thr Asn Ala Thr Gly Phe Ile Ser Tyr Tyr Glu Ile Cys
305                 310                 315                 320

Leu Glu Val Asp Asp Pro Ser Lys Gly Trp Thr Lys Lys Trp Asp Glu
                325                 330                 335

His Gly Lys Val Pro Tyr Ala Tyr Lys Gly Asn Gln Trp Val Gly Tyr
            340                 345                 350

Glu Asp Pro Lys Ser Val Ala Leu Lys Met Glu Phe Ile Lys Ser Lys
        355                 360                 365

Gly Tyr Gly Gly Ala Met Thr Trp Ala Ile Asp Met Asp Asp Phe Gln
370                 375                 380

Gly Val Cys Ser Asp Asp Lys His Thr Leu Ala Val Ile Met His Asp
385                 390                 395                 400

Tyr Met Lys Asn Tyr Ile Val Pro Glu Phe Asp Ser Ser Arg Ile Thr
                405                 410                 415

Pro Arg Pro Glu Trp Ala Lys Pro Pro Ser Thr Pro Ser Gln Glu Pro
            420                 425                 430

Asp Asp Thr Pro Tyr Ile Pro Thr Thr His Ala Pro Lys Pro Ser Arg
        435                 440                 445

Lys Pro Thr Arg Lys Pro Lys Pro Thr Thr Thr Thr Val Ala Ala Thr
450                 455                 460

Thr Pro Val Ala Thr Thr Thr Thr Glu His His His His His His Glu
465                 470                 475                 480
```

```
Glu Glu Lys Pro Ser Glu Gln Asp Asn Gln Val Gly Ser Gln Asp Thr
                485                 490                 495

Thr Ala Thr Asp Val Asp Cys Ser Gln Glu Asp Tyr Leu Pro His Glu
            500                 505                 510

Asp Cys Asn Lys Tyr Tyr Arg Cys Val His Gly Glu Ala Val Leu Phe
            515                 520                 525

Thr Cys Arg Glu Gly Thr Val Tyr His Thr Ile Ser His Val Cys Asp
        530                 535                 540

Trp Ala Ser Asn Ser Asp Arg Glu Arg Cys Arg Asp Leu Lys Ser Val
545                 550                 555                 560

Pro Pro Pro Lys Leu Leu Thr Asp Glu Glu Ile Ala Asn Lys Leu Ser
                565                 570                 575

Lys Tyr Ile Asp Leu Pro Ile Leu Gly Ser Thr Ser Pro Val Trp Trp
            580                 585                 590

Asn Ser Ala Asp Ile Gln His Ser Gly Gly Arg Ser Ser Leu Glu Gly
            595                 600                 605

Pro Arg Phe Glu Gly Lys Pro Ile Pro Asn Pro Leu Leu Gly Leu Asp
        610                 615                 620

Ser Thr Arg Thr Gly His His His His His His
625                 630                 635

<210> SEQ ID NO 33
<211> LENGTH: 1919
<212> TYPE: DNA
<213> ORGANISM: Tagged Ctenocephalides felis

<400> SEQUENCE: 33
tcaatggtga tggtgatgat gaccggtacg cgtagaatcg agaccgagga gagggttagg      60
gataggctta ccttcgaacc gcgggccctc tagactcgag cggccgccac tgtgctggat     120
atctgcagaa ttccaccaca ctggactagt ggatcccaat ataggtaagt caatatattt     180
cgatagttta ttagctattt cttcatcagt caataatttt ggaggtggaa cgcttttttaa    240 gtctcgacat ctttctctgt ctgaattcga tgcccaatca caaacgtggc ttatggtgtg     300
gtaaacggtt ccttctcgac aagtgaagag aactgcttct ccgtggacac aacggtaata     360
cttgttgcaa tcctcatgag gcaaatagtc ttcctgcgaa caatctacat cagttgcagt     420
agtatcttgg ctaccaactt ggttgtcctg ttcgctcggc ttctcttctt cgtgatggtg     480
gtgatggtgt tctgtagtcg ttgtggcaac aggagtggtt gccgccacag ttgtggttgt     540
tggtttcggt tttctggttg gtttgcggct cggttttggt gcgtgggttg tgggaatgta     600
tggtgtgtcg tctggttctt gtgaaggagt gcttggtggt tttgcccatt caggcctggg     660
agtaatccga ctcgaatcaa attcaggaac aatataattc ttcatgtaat cgtgcatgat     720
gaccgccaag gtgtgtttgt catcagagca tactccttgg aaatcgtcca tgtcgatggc     780
ccaagtcatg gcacctccat aacccttaga tttaataaat tccatcttca gagccacgga     840 tttttgggtct tcgtagccaa cccattgatt tcctttataa gcatatgcca cttttccatg    900
ttcgtcccat tttttagtcc agcctttgga aggatcatca acttctaagc atatctcata     960
ataagaaata atccggtag cgttagtgta aggtccaggt tcacctcctc cagcttcttt     1020
gttgatgtag gttcccaacc tgtagtcctt attgctgttg ctcaatgtga agaatcttcc    1080
ataaaatgga acaccaacga ccaacttgtt tgctggacaa cccatatcaa cccataattg    1140
taatccatca ttcacattga gtttctcata agcatattga tcatgtggcc ttctgtacaa    1200
gggactgtgg gtatcagcaa accctgccca atttcctctc aaatcgtaag acattacgtg    1260
```

```
gatagcatct aataattcgc aaagttctgg tacatgatat ccttcctgca gcctaaattt   1320
ggcaatcggg acagccatgg tgatctccca gttttttgcct tgtttgttga aagcccttcg   1380
caattcttgg acaaagtata aaatttgtc tttgtcggaa aaactgccac ctctatcagc   1440
agcaccagga tactcccaat ccaagtcgaa accgtcgaac ttgtattcgt tcatgaaatc   1500
aactacactg cgaataaagg ctgatctctt cctcttttcg gccaccatgg tcgaatattt   1560
ttttccgcct tcagcccatc ctccgacggc tatttgtaat ttcacatttg gatgaatttt   1620
tctcaaattt gtgaaattct tgaaaccatt gtcatctatg tccaactctg ggtcgatgac   1680
cagcacgctc cagtctttgt cgtctactcc gatgaaagaa taaactatat gggtacacaa   1740
gtcaactggt atgtcctcta tgccatatct gcctattccg ggcctgtaaa ctgcccaatt   1800
gctgaagtaa catactatcc tggccttctg gtctgatgct tcaactgtat taattgaaga   1860
gattgctatg gcgcacaaaa cggctaacaa gttccagtgt cttcccattt caagcttaa   1919
```

```
<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
aaggatccgg tgaaattaca aatagccg                                        28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
ttctcgagtt ataagtctcg acatctttc                                       29

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ttaagcttga aatgggaaga cactggaact tgttag                               36

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
ttggatccca atataggtaa gtcaatatat ttc                                  33

<210> SEQ ID NO 38
<211> LENGTH: 36
<212> TYPE: DNA
```

```
<213> ORGANISM: Artificial Sequence
<220> FEATURE:
<223> OTHER INFORMATION: Description of Artificial Sequence:  Synthetic
      Primer

<400> SEQUENCE: 38 ttggatccttt acaatatagg taagtcaata tatttc                              36

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 39
rccatrtcwa twgccca                                                    17

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 40
cgctctagaa ctagtggatc                                                 20
```

FLEA CHITINASE NUCLEIC ACID MOLECULES AND USES THEREOF

CROSS-REFERENCE TO RELATED APPLICATIONS

This application claims priority to U.S. Provisional Application Serial No. 60/128,833, filed Apr. 9, 1999 entitled "FLEA CHITINASE NUCLEIC ACID MOLECULES, PROTEINS AND USES THEREOF".

FIELD OF THE INVENTION

The present invention relates to flea chitinase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from flea infestation.

BACKGROUND OF THE INVENTION

Flea infestation in animals is a health and economic concern because fleas are known to cause and/or transmit a variety of diseases. Fleas directly cause a variety of diseases, including allergies, and also carry a variety of infectious agents including, but not limited to, endoparasites (e.g., nematodes, cestodes, trematodes and protozoa), bacteria and viruses. In particular, the bites of fleas are a problem for animals maintained as pets because the infestation becomes a source of annoyance not only for the pet but also for the pet owner who may find his or her home generally contaminated with fleas. As such, fleas are a problem not only when they are on an animal but also when they are in the general environment of the animal.

Bites from fleas are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of flea infestation has prompted the development of reagents capable of controlling flea infestation. Commonly encountered methods to control flea infestation are generally focused on use of insecticides. While some of these products are efficacious, most, at best, offer protection of a very limited duration. Furthermore, many of the methods are often not successful in reducing flea populations. In particular, insecticides have been used to prevent flea infestation of animals by adding such insecticides to shampoos, powders, collars, sprays, spot-on formulations, foggers and liquid bath treatments (i.e., dips). Reduction of flea infestation on the pet has been unsuccessful for one or more of the following reasons: failure of owner compliance (frequent administration is required); behavioral or physiological intolerance of the pet to the pesticide product or means of administration; and the emergence of flea populations resistant to the prescribed dose of pesticide.

Insect chitinases play an important role in molting and cuticle turnover by hydrolyzing the structural polymer chitin (poly-β-(1,4)-N-acetyl-D-glucosamine), a principal component of the insect exoskeleton and gut lining. Chitinase activity has been identified in the molting fluids and midguts of several insects; examples include *Bombyx mori, Manduca sexta, Aedes aegypti*, and the wasp Chelonus. Chitinase appears to play an important role in insect growth and development; for example chitinase is essential for the removal and remodeling of old cuticle during metamorphosis of insects from one stage to the next. Inhibition of flea chitinase offers the potential of disrupting flea growth and development, thereby killing the fleas. However, development of flea chitinase inhibitors to disrupt flea growth and development, thereby reducing flea infestation, has been hampered by the lack of the appropriate reagent, i.e. flea chitinase.

Prior investigators have described the following insect chitinase nucleic acid sequences: *Aedes Aegypti* chitinase cDNA, Specht, (1997) et al. direct submission to Genbank, accession number AF02649 1; *Manduca sexta* chitinase precursor mRNA, Muthukrishnan, (1998) direct submission to Genbank, accession number U02270; *Bombyx mori* chitinase mRNA, Kim, M. K.et al. (1997) direct submission to Genbank, accession number BMU86876. Prior investigators have also described the following insect chitinase polypeptides: the endochitinase precursor from *Manduca sexta*, Choi, et al. (1997) *Insect Biochem. Mol. Biol.* 27(1), p 37–47; chitinase-like protein from *Bombyx mori*, Kim, et al. (1997), accession number 18418551; chitinase protein from *Hyphantria cunea*, Kim, et al. (1997), accession number 1841853; chitinase from *Aedes aegypti*, Specht et al. (1997), direct submission to Genbank, accession number 2564719; chitinase protein from *Drosophila melanogaster*, Genbank accession number JC4038; chitinase protein from *Chironomus tentans*, Genbank accession number Y13233; chitinase protein from Chelonus (sp), Genbank accession number A53918; chitinase protein from *Anopheles freeborni*, Genbank accession number AF026495; chitinase protein from *Anopheles gambiae*, Genbank accession number AF008575; and chitinase protein from *Phaedon cochleariae*, Genbank accession number Y 18011.

Identification of flea chitinase proteins and nucleic acids of the present invention is surprising, because overall homology of the flea chitinase to other insect chitinases that have been described is fairly low. The highest identity between a flea chitinase of the present invention and the protein that most closely resembles the flea chitinase in the databases searched is only 64%. Homologies between deduced insect chitinase proteins described to date have typically been greater; for example, amino acid alignment homology of three insect chitinases is 75% between *Bombyx mori* and *Hyphantria cunea*, 80% between *B. mori* and *Manduca sexta*, and 77% between *H. cunea* and *M. sexta*. See Kim, et al., (1998), *Insect Biochemistry and Molecular Biology*, vol 28 pp 163–171.

Identification of a flea chitinase is also surprising, because of the rarity of the mRNA coding for chitinase from the cDNA libraries made from various larval stages. It has been found that in other insects, expression of chitinase is very tightly regulated, and is restricted to short time intervals, such as when molting events are initiating. Since fleas are so small, and have much less RNA, compared to other insects that are traditionally studied, i.e. *Bombyx mori*, the silkworm, and *Manduca sexta*, the tobacco homworm, obtaining sufficient numbers of fleas synchronized to the exact right life stage where chitinase is being expressed is very difficult.

Thus, there remains a need to develop a flea chitinase reagent and a method to protect animals from flea infestation by targeting flea chitinase.

SUMMARY OF THE INVENTION

The present invention relates to a novel product and process for protection of animals from flea infestation.

Identification of flea chitinase proteins and nucleic acid molecules of the present invention is surprising, however, due to the low degree of homology of flea chitinase to chitinases described from other insects, and due to the difficulty in obtaining fleas in the proper life stage, such that the fleas are expressing chitinase.

According to the present invention there are provided flea chitinase proteins, and mimetopes thereof; flea chitinase nucleic acid molecules, including those that encode such proteins; antibodies raised against such flea chitinase proteins (i.e., anti-flea chitinase antibodies); and compounds that inhibit flea chitinase activity (i.e., inhibitory compounds or inhibitors).

The present invention also includes methods to obtain such proteins, mimetopes, nucleic acid molecules, antibodies and inhibitory compounds. Also included in the present invention are therapeutic compositions comprising a nucleic acid molecule, protein, mimetope, and/or protective compound derived from a protein of the present invention that inhibits the activity of flea chitinase.

One embodiment of the present invention is an isolated nucleic acid molecule that is selected from a group consisting of (a) a nucleic acid molecule that includes one or more of the following sequences: SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO: 13, SEQ ID NO:15, SEQ ID NO:16, SEQ ID NO:18, SEQ ID NO:25, and SEQ ID NO:27; and (b) a nucleic acid molecule comprising an at least a consecutive 18 nucleotide portion identical in sequence to a consecutive 18 nucleotide portion of a sequence as set forth in (a).

In another embodiment of the present invention, an isolated nucleic acid molecule is selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27; and/or a nucleic acid molecule comprising an allelic variant of a nucleic acid sequence described above.

Another embodiment of the present invention is a nucleic acid molecule which is selected from the group consisting of (a) a nucleic acid molecule that encodes a protein comprising an amino acid sequence selected from the group consisting of SEQ ID NO:2, SEQ ID NO:5, SEQ ID NO:8, SEQ ID NO:1, SEQ ID NO:14, SEQ ID NO:17 and/or SEQ ID NO:26; (b) a nucleic acid molecule that encodes a protein comprising an at least 25 consecutive amino acid residue portion identical in sequence to a consecutive 25 amino acid residue of a sequence as set forth in (a); (c) a nucleic acid molecule that encodes a protein comprising a fragment of a protein as set forth in (a), wherein the fragment has chitinase activity; and (d) an allelic variant of a nucleic acid molecule that encodes any protein of (a), (b), or (c). Chitinase activity can include binding to a chitin molecule and/or hydrolyzing a chitin molecule. In another embodiment, the nucleic acid molecule is selected from the group consisting of a nucleic acid molecule comprising a nucleic acid sequence encoding a protein comprising an amino acid sequence selected from the group consisting of SEQ ID NO:2, SEQ ID NO:5, SEQ ID NO:8, SEQ ID NO:11, SEQ ID NO:14, SEQ ID NO:17, and/or SEQ ID NO:26, and a nucleic acid molecule comprising an allelic variant of a nucleic acid molecule encoding any of such amino acid sequences.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

In another embodiment, there is provided an isolated protein that can be any of the following: (a) a protein including one or more of the following amino acids: SEQ ID NO:2, SEQ ID NO:5, SEQ ID NO:8, SEQ ID NO:1, SEQ ID NO:14, SEQ ID NO:17, and SEQ ID NO:26; (b) a protein comprising an at least 25 consecutive amino acid portion identical in sequence to a consecutive 25 amino acid portion of a sequence as set forth in (a); (c), a protein comprising a fragment of (a) above, wherein said fragment has chitinase activity; and/or (d), a protein encoded by an allelic variant of a nucleic acid molecule encoding any of the above proteins. Another embodiment includes an isolated antibody that selectively binds to a protein of the present invention. The present invention also relates to mimetopes of flea chitinase proteins as well as mimetopes of isolated antibodies that selectively bind to flea chitinase proteins. Also included are methods, including recombinant methods, to produce proteins, antibodies, and mimetopes of the present invention.

One embodiment of the present invention is a therapeutic composition that, when administered to an animal susceptible to flea infestation, reduces flea infestation present in said animal. Such a therapeutic composition includes at least one of the following protective molecules: (a) an isolated flea chitinase protein of the present invention; (b) a mimetope of an isolated flea chitinase protein of the present invention; (c) an isolated flea chitinase nucleic acid molecule of the present invention; and (d) a molecule derived from an isolated flea chitinase protein that inhibits chitinase activity. Examples of such protective molecules include, but are not limited to, a substrate analog of flea chitinase, an isolated antibody that selectively binds to a flea chitinase protein, other organic or inorganic molecules that inhibit chitinase activity, a naked nucleic acid vaccine, a recombinant virus vaccine, a recombinant cell vaccine, and a recombinant protein vaccine. A therapeutic composition of the present invention can further comprise an excipient, a carrier, and/or an adjuvant.

Another embodiment of the present invention includes a method to reduce flea infestation in an animal. Such a method includes the step of administering to the animal a therapeutic composition of the present invention.

Another embodiment of the present invention includes a method to identify a compound capable of inhibiting the activity of flea chitinase. Such a method includes the steps of: (a) contacting an isolated flea chitinase protein of the present invention with a putative inhibitory compound under conditions in which, in the absence of the putative inhibitory compound, the protein has chitinase activity, and (b) determining if the putative inhibitory compound inhibits chitinase activity.

In another embodiment of the present invention, an assay kit is provided to identify an inhibitor of a flea chitinase. The assay kit comprises an isolated flea chitinase protein of the present invention and a means for determining inhibition of an activity of flea chitinase. Such a means enables the detection of inhibition, wherein detection of inhibition identifies an inhibitor of flea chitinase activity.

DETAILED DESCRIPTION OF THE INVENTION

The present invention provides for isolated flea chitinase proteins, isolated flea chitinase nucleic acid molecules, isolated antibodies directed against flea chitinase proteins, and compounds able to inhibit flea chitinase function (i.e., inhibitory compounds). The present invention also provides for methods to reduce flea infestation by administering to an animal susceptible to flea infestation a therapeutic composition derived from a protein of the present invention, and methods to identify an inhibitory compound capable of inhibiting the activity of flea chitinase. As used herein, the terms isolated flea chitinase proteins and isolated flea chitinase nucleic acid molecules refer to chitinase proteins and chitinase nucleic acid molecules derived from fleas; as such the proteins and nucleic acid molecules can be isolated from fleas or prepared recombinantly or synthetically. Flea chitinase nucleic acid molecules of known length isolated from *Ctenocephalides felis* are denoted "nCfCHT$_\#$", for example nCfCHT$_{2610}$, wherein "#" refers to the number of nucleotides in that molecule, and CHT proteins of known length are denoted "PCfCHT$_\#$" (for example PCfCHT$_{583}$) wherein "#" refers to the number of amino acid residues in that molecule.

Flea chitinase proteins and nucleic acid molecules of the present invention have utility because they represent novel targets for anti-arthropod vaccines and chemotherapeutic drugs. The products and processes of the present invention are advantageous because they enable the inhibition of arthropod development, metamorphosis, feeding, and/or digestion processes that involve chitinase proteins. Chitinase activity has been identified in the molting fluids and midguts of several insects, as mentioned previously. In the midgut of several insects, chitin lines the surface of the gut, and chitinase is thought to play a role in degrading gut chitin. For example, chitinase may be involved in allowing expansion of the gut after a blood meal and also may assist in digestion. The present invention also indicates that flea chitinase activity occurs in extracts of fleas from various developmental stages; see Examples. Expression of flea chitinase has been shown to be most predominant in flea larval and pupal stages. Thus there are opportunities to intervene in flea development and/or digestion using embodiments of the present invention. The present invention is particularly advantageous because the proteins of the present invention have not been found in vertebrates; thus chitinase inhibitors, whether chemical compounds or antibodies against native protein, may not pose a potential health hazard to pets or to pet owners.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain flea chitinase proteins and nucleic acids of the present invention include, but are not limited to, fed third instar larvae, fed wandering larvae, fed prepupal larvae, and fed pupae.

One embodiment of the present invention is an isolated protein that includes a flea chitinase protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

Preferred fleas from which to isolate chitinase proteins or nucleic acid molecules include Ctenocephalides, Ceratophyllus, Diamanus, Echidnophaga, Nosopsyllus, Pulex, Tunga, Oropsylla, Orchopeus and Xenopsylla. More preferred fleas include *Ctenocephalides felis, Ctenocephalides canis, Ceratophyllus pulicidae, Pulex irritans, Oropsylla (Thrassis) bacchi, Oropsylla (Diamanus) montana, Orchopeus howardi, Xenopsylla cheopis* and *Pulex simulans*, with *C. felis* being even more preferred. Such fleas are also preferred targets for therapeutic compositions of the present invention.

As used herein, isolated flea chitinase proteins of the present invention can be full-length proteins or any homolog of such proteins. An isolated protein of the present invention, including a homolog, can be identified in a straight-forward manner by the protein's ability to elicit an immune response against a flea chitinase protein or by the protein's chitinase activity. Examples of flea chitinase homolog proteins include flea chitinase proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a flea chitinase protein, and/or of binding to an antibody directed against a flea chitinase protein. That is, when the homolog is administered to an animal as an immunogen, using techniques known to those skilled in the art, the animal will produce an immune response against at least one epitope of a natural flea chitinase protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids in length.

In one embodiment of the present invention a flea homolog protein has chitinase activity. Examples of flea chitinase activity include binding to a chitin molecule and hydrolyzing a chitin molecule. Examples of methods to detect chitinase activity are disclosed herein.

Flea chitinase homolog proteins can be the result of natural allelic variation or natural mutation. Flea chitinase protein homologs of the present invention can also be produced using techniques known in the art including, but not limited to, direct modifications to the protein or modifications to the gene encoding the protein using, for example, classic or recombinant DNA techniques to effect random or targeted mutagenesis.

Flea chitinase proteins of the present invention are encoded by flea chitinase nucleic acid molecules. As used herein, flea chitinase nucleic acid molecules include nucleic acid sequences related to natural flea chitinase genes, and, preferably, to Ctenocephalides felis chitinase genes. As used herein, flea chitinase genes include all regions such as regulatory regions that control production of flea chitinase proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons, such as is often found for flea genes. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a flea chitinase gene that includes one or more of the following nucleic acid sequences: nucleic acid sequence SEQ ID NO:1, SEQ ID NO:4, SEQ ID NO:7, SEQ ID NO:10, SEQ ID NO:13, SEQ ID NO:16, and/or SEQ ID NO:25, as well as the complements of any of these nucleic acid sequences, including SEQ ID NO:3, SEQ ID NO:6, SEQ ID NO:9, SEQ ID NO:12, SEQ ID NO:15, SEQ ID NO:18, and/or SEQ ID NO:27. Nucleic acid sequence SEQ ID NO:1 and its complement SEQ ID NO:3 represent an apparently 5' truncated version of a C. felis chitinase cDNA; and SEQ ID NO:7 and its complement SEQ ID NO:9 represent a RACE clone that includes the 5' end of a C. felis chitinase cDNA. These nucleic acid sequences are further described herein, and the cloning of the corresponding nucleic acid molecules is described in the Examples. The complement of SEQ ID NO:1, represented herein by SEQ ID NO:3, refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to, i.e. can form a complete double helix with, the strand for which the sequence is cited. It should be noted that since nucleic acid sequencing technology is not entirely error-free, SEQ ID NO:1 represents an apparent nucleic acid sequence of the nucleic acid molecule encoding a chitinase protein of the present invention; such is also the case for other nucleic acid and protein sequences presented herein.

The nucleic acid sequences of the coding strand and complementary strand of nCfCHT$_{2610}$ are represented herein as SEQ ID NO:1 and SEQ ID NO:3, respectively. Translation of SEQ ID NO:1 suggests that nucleic acid molecule nCfCHT$_{2610}$ encodes a full-length chitinase protein of 583 amino acids, denoted herein as PCfCHT$_{583}$, the amino acid sequence of which is presented in SEQ ID NO:2, assuming an open reading frame spanning from nucleotide 1 through nucleotide 1749 of SEQ ID NO:1. The coding region encoding PCfCHT$_{583}$, without the stop codon, is presented herein as nCfCHT$_{1749}$, which has the nucleotide sequence SEQ ID NO:4 (the coding strand) and SEQ ID NO:6 (the complementary strand). Translation of SEQ ID NO:4 yields SEQ ID NO:5 (the same sequence as SEQ ID NO:2), assuming a first in-frame codon extending from nucleotide 1 to nucleotide 3 of SEQ ID NO:4. nCfCHT$_{405}$, a flea chitinase nucleic acid molecule obtained by RACE (Rapid Amplification of cDNA Ends), has a nucleic acid sequence denoted by SEQ ID NO:7, the coding strand, and SEQ ID NO:9, the complementary strand. Translation of SEQ ID NO:7 suggests that nucleic acid molecule nCfCHT$_{405}$ encodes a partial length chitinase protein of 117 amino acids, denoted herein as PCfCHT$_{117}$, the amino acid sequence of which is presented as SEQ ID NO:8. The open reading frame of SEQ ID NO:7 is denoted SEQ ID NO:10, as the coding strand of nCfCHT$_{351}$, and extends from nucleotide 55 to nucleotide 405 of SEQ ID NO:7, which encodes a partial length chitinase protein of 117 amino acids, denoted herein as PCfCHT$_{117}$, the amino acid sequence of which is represented by SEQ ID NO:11, which is the same sequence as SEQ ID NO:8. nCfCHT$_{351}$, also has a complementary strand, denoted herein as SEQ ID NO:12. Flea chitinase nucleic acid molecule nCfCHT$_{115}$, a PCR product derived from hybridization of a C. felis wandering larvae and mixed instar cDNA library with primers SEQ ID NO:19 and SEQ ID NO:20, has a nucleic acid sequence represented by SEQ ID NO:16 and a complementary strand represented by SEQ ID NO:18. Translation of SEQ ID NO:16, assuming a first in-frame codon extending from nucleotide 2 to nucleotide 4, suggests that nCfCHT$_{115}$ encodes a partial length chitinase protein of 38 amino acids, also known as PCfCHT$_{38}$, having SEQ ID NO:17.

Sequence analysis of SEQ ID NO:2 revealed the following features: a putative signal sequence, extending from about residue 1 to about residue 24, serving to direct the chitinase to be exported from the cell; and a putative mature protein, arising after cleavage of the signal sequence, extending from about residue 25 to about residue 583. Within the mature protein, a putative endochitinase domain extends from about residue 25 to about residue 381, a putative PEST region extends from about residue 399 to about residue 500, and a cysteine-rich putative chitin-binding domain extends from about residue 501 to about residue 556. The open reading frame encoding the mature chitinase protein sequence is denoted nCfCHT$_{1677}$, having a coding strand of SEQ ID NO:13, and a complement denoted SEQ ID NO:15; and the mature chitinase protein sequence is denoted PCfCHT$_{559}$, having the amino acid sequence represented by SEQ ID NO:14. The RACE cDNA clone, nCfCHT$_{405}$, encodes part of a mature chitinase protein; this protein, denoted as PCfCHT$_{92}$, has an amino acid sequence represented by SEQ ID NO:26, which is coded for by a nucleic acid molecule denoted nCHT$_{276}$, having a coding strand sequence of SEQ ID NO:25, and a complement sequence of SEQ ID NO:27.

In another embodiment, a chitinase gene or other nucleic acid molecule can be an allelic variant that includes a similar but not identical sequence to SEQ ID NO:1, and/or SEQ ID NO:4, or any other flea chitinase nucleic acid sequence cited herein. For example, an allelic variant of a C. felis chitinase gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea such as C. felis, since the genome is diploid, and sexual reproduction will result in the reassortment of alleles. One potential example of an allelic variant of SEQ ID NO:1 is SEQ ID NO:7, as described in the Examples.

In one embodiment of the present invention, isolated chitinase proteins are encoded by nucleic acid molecules that hybridize under stringent hybridization conditions to genes or other nucleic acid molecules encoding flea chitinase proteins respectively. The minimal size of chitinase proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea chitinase nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea chitinase protein is typically at least about 12 to about 15 nucleotides in length if the nucleic acid molecule is GC-rich and at least about 15 to about 18 bases in length if it is AT-rich. The minimal size of a nucleic acid molecule used to encode a flea chitinase protein homolog of the present invention is from about 12 to about 18 nucleotides in length. Thus, the minimal size of chitinase protein homologs of the present invention is from about 4 to about 6 amino acids in length. There is no limit, other than a practical limit, on the maximal size of a nucleic acid molecule encoding a flea chitinase protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as formamide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° \text{ C.} + 16.6 \log M + 0.41(\%G+C) - 500/n - 0.61(\%\text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% or less base pair mismatch, i.e., at least about 70% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea nucleic acid molecule of about 150 bp in length or greater, the following conditions could preferably be used. The average G+C content of flea DNA is about 37%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC and 0% formamide, the $T_m$ of perfect hybrids would be about 77° C.:

$$81.5° C.+16.6 \log (0.15M)+(0.41\times0.37)-(500/150)-(0.61\times0)=77.5° C.$$

Thus, to achieve hybridization with nucleic acid molecules having about 30% base pair mismatch, hybridization washes would be carried out at a temperature of less than or equal to 47.5° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 47.5° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™, available from Genetics Computer Group, Madison, Wis., DNAsis™, available from Hitachi Software, San Bruno, Calif., and MacVector™, available from the Eastman Kodak Company, New Haven, Conn. A preferred method to determine percent identity among amino acid sequences and also among nucleic acid sequences includes using the GAP program with pair-wise comparisons within the program GCG™ Version 9.0-UNIX, hereinafter referred to as default parameters.

A preferred flea chitinase protein includes a protein encoded by a nucleic acid molecule of length equal to or greater than 150 nucleotides that hybridizes under conditions which preferably allow for less than or equal to about a 30% base pair mismatch, and even more preferably under conditions which allow for less than or equal to about a 20% base pair mismatch with a nucleic acid molecule selected from the group consisting of SEQ ID NO:3, SEQ ID NO:6, SEQ ID NO:9, SEQ ID NO:12, SEQ ID NO:15, SEQ ID NO:18, and/or SEQ ID NO:27.

Another preferred flea chitinase protein of the present invention includes proteins that are preferably at least about 70% identical, more preferably at least about 75%, more preferably at least about 80%, more preferably at least about 85%, more preferably at least about 90%, more preferably at least about 95%, and even more preferably at least about 100% identical to $PCfCHT_{583}$, $PCFCHT_{117}$, $PCfCHT_{559}$, $PCfCHT_{92}$, and/or $PCfCHT_{38}$. Also preferred are proteins encoded by allelic variants of a nucleic acid molecule encoding protein $PCfCHT_{583}$, $PCfCHT_{117}$, $PCfCHT_{559}$, $PCfCHT_{92}$, and/or $PCfCHT_3$. Percent identity as used herein is determined using the Compare function by maximum matching within the program GCG™ Version 2.1 using default parameters.

As such, preferred chitinase proteins of the present invention include proteins having amino acid sequences that are preferably at least about 70%, preferably at least about 75%, preferably at least about 80%, more preferably at least about 85%, more preferably at least about 90%, more preferably at least about 95%, and even more preferably at least about 100% identical to an amino acid sequence selected from the group consisting of SEQ ID NO:2, SEQ ID NO:5, SEQ ID NO:8, SEQ ID NO:11, SEQ ID NO:14, SEQ ID NO:17, and/or SEQ ID NO:26, and chitinase proteins encoded by allelic variants of nucleic acid molecules encoding chitinase proteins having amino acid sequences SEQ ID NO:2, SEQ ID NO:5, SEQ ID NO:8, SEQ ID NO:11, SEQ ID NO:14, SEQ ID NO:17 and/or SEQ ID NO:26.

A preferred isolated protein of the present invention is (a) a protein having nucleic acid sequence SEQ ID NO:2, SEQ ID NO:5, SEQ ID NO:8, SEQ ID NO:11, SEQ ID NO:14 SEQ ID NO:17, and/or SEQ ID NO:26, (b) a protein comprising an at least 25 consecutive amino acid portion identical in sequence to a consecutive 25 amino acid portion of a sequence as set forth in (a); (c), a protein comprising a fragment of a sequence as set forth in (a), wherein the fragment has an activity selected from the group consisting of binding to a chitin molecule and hydrolyzing a chitin molecule; and (d) a protein encoded by an allelic variant of a nucleic acid molecule that encodes any protein of (a), (b), or (c). A protein comprising an at least 25 consecutive amino acid portion identical in sequence to a consecutive 25 amino acid portion of SEQ ID NO:2, SEQ ID NO:5, SEQ ID NO:8, SEQ ID NO:11, SEQ ID NO:14, SEQ ID NO:17 and/or SEQ ID NO:26 refers to a 25 amino acid protein that is identical in sequence to (i.e. share 100% sequence identity with) a 25-amino acid portion of one of the named sequences above, as well as to proteins that have amino acid residues) that extend from both or either of the N-terminal and/or C-terminal end(s) of the consecutive identical 25-amino acid portion. The N-terminal and/or C-terminal extensions can include one or more extensions that have no identity to a flea chitinase of the present invention, as well as one or more extensions that show similarity or identity to cited amino acid sequences or portions thereof.

A preferred isolated protein of the present invention is a protein encoded by at least one of the following nucleic acid molecules: $nCfCHT_{2610}$, $nCfCHT_{1749}$, $nCfCHT_{405}$, $nCfCHT_{351}$, $nCfCHT_{1677}$, $nCfCHT_{276}$, and/or $nCfCHT_{115}$, or allelic variants of any of these nucleic acid molecules. As such, a preferred isolated protein is encoded by a nucleic acid molecule having nucleic acid sequence SEQ ID NO:1, SEQ ID NO:4 SEQ ID NO:7, SEQ ID NO:10, SEQ ID NO:13, SEQ ID NO:16, and/or SEQ ID NO:25, or a protein encoded by an allelic variant of any of these listed nucleic acid molecules.

In one embodiment of the present invention, flea chitinase proteins comprise amino acid sequences SEQ ID NO:2, SEQ ID NO:5, SEQ ID NO:8, SEQ ID NO:11, SEQ ID NO:14 SEQ ID NO:17, and/or SEQ ID NO:26, including, but not limited to, the proteins consisting of the cited amino acid sequences, fusion proteins and multivalent proteins and proteins encoded by allelic variants of nucleic acid molecules encoding proteins having amino acid sequence SEQ ID NO:2, SEQ ID NO:5, SEQ ID NO:8, SEQ ID NO:11, SEQ ID NO:14, SEQ ID NO:17, and/or SEQ ID NO:26.

A preferred flea chitinase protein includes a protein encoded by a nucleic acid molecule which hybridizes under conditions which preferably allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch and even more preferably under conditions which allow about 5% or less base pair mismatch with a nucleic acid molecule selected from the group consisting of SEQ ID: 3, SEQ ID NO:6, SEQ ID NO:9, SEQ ID NO:12, SEQ ID NO:15, SEQ ID NO:18, and/or SEQ ID NO:27.

Another embodiment of the present invention includes a flea chitinase protein encoded by a nucleic acid molecule, wherein said nucleic acid molecule hybridizes, in a solution comprising 1×SSC and 0% formamide, at a temperature of about 47.5° C., to an isolated nucleic acid molecule selected from the group consisting of SEQ ID: 3, SEQ ID NO:6, SEQ ID NO:9, SEQ ID NO:12, SEQ ID NO:15, SEQ ID NO:18, and/or SEQ ID NO:27.

In one embodiment, a preferred flea chitinase protein comprises an amino acid sequence of at least about 25 amino acids, or at least about 30 amino acids, or at least about 50 amino acids, or at least about 70 amino acids, or at least about 90 amino acids, or at least about 110 amino acids, or at least about 130 amino acids, or at least about 150 amino acids, or at least about 170 amino acids, or at least about 190 amino acids, or at least about 210 amino acids, or at least about 230 amino acids, or at least about 250 amino acids, or at least about 270 amino acids, or at least about 290 amino acids, or at least about 310 amino acids, or at least about 330 amino acids, or at least about 350 amino acids, or at least about 370 amino acids, or at least about 390 amino acids, or at least about 410 amino acids, or at least about 430 amino acids, or at least about 450 amino acids, or at least about 470 amino acids, or at least about 490 amino acids, or at least about 510 amino acids, or at least about 530 amino acids, or at least about 550 amino acids, or at least about 570 amino acids, or at least about 580 amino acids. In another embodiment, preferred flea chitinase proteins comprise full-length proteins, i.e., proteins encoded by full-length coding regions, or post-translationally modified proteins thereof, such as mature proteins from which initiating methionine and/or signal sequences have been removed.

Additional preferred flea chitinase proteins of the present invention include proteins having the amino acid sequence SEQ ID NO:2 SEQ ID NO:5, SEQ ID NO:8, SEQ ID NO:11, SEQ ID NO:14, SEQ ID NO:17, and/or SEQ ID NO:26, and proteins comprising homologs thereof, wherein such a homolog comprises at least one epitope that elicits an immune response against a protein having an amino acid sequence SEQ ID NO:2, SEQ ID NO:5, SEQ ID NO:8, SEQ ID NO:11, SEQ ID NO:14, SEQ ID NO:17, and/or SEQ ID NO:26. Likewise, also preferred are proteins encoded by nucleic acid molecules comprising nucleic acid sequence SEQ ID NO:1, SEQ ID NO:4, SEQ ID NO:7, SEQ ID NO:10, SEQ ID NO:13, SEQ ID NO:16, and/or SEQ ID NO:25, or by homologs thereof.

For a protein to have chitinase activity, the protein must have one or more functional chitinase domain(s). A functional chitinase domain is at least the smallest piece, or fragment, of the protein that is necessary to allow the protein to have chitinase activity. For example, a functional domain also includes proteins that are larger than the smallest fragment necessary to allow chitinase activity. Examples of chitinase functional domains are chitin binding domains and domains that hydrolyze chitin.

One of skill in the art will understand that a nucleic acid molecule or protein fragment of the present invention is an example of a homolog that includes a portion of a larger nucleic acid molecule or protein, respectively. One of skill in the art will also understand that fragments including one or more of the functional domains of chitinase can vary and extend beyond those particular nucleic acid or amino acid regions defined herein. Nucleic acids or amino acids essential to an active domain can be identified using standard protein or DNA binding assays known to those of skill in the art to determine whether an active domain has chitinase activity.

In another embodiment, a preferred flea chitinase protein of the present invention is encoded by a nucleic acid molecule comprising apparently full-length chitinase coding regions, e.g., nucleic acid molecules encoding an apparently full-length chitinase protein or a post-translationally modified version thereof. Also preferred is a flea chitinase protein that includes the endochitinase domain and/or chitin binding domain. In another embodiment, a preferred chitinase protein of the present invention is encoded by a nucleic acid molecule comprising at least about 18 nucleotides, at least about 20 nucleotides, at least about 30 nucleotides, at least about 40 nucleotides, at least about 100 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1100 nucleotides, at least about 1200 nucleotides, at least about 1300 nucleotides, at least about 1400 nucleotides, at least about 1500 nucleotides, at least about 1600 nucleotides, at least about 1700 nucleotides, and more preferably at least about 1677 or 1749 nucleotides in length. Within this embodiment is an chitinase protein encoded by at least a portion of nCfCHT$_{2610}$, nCfCHT$_{1749}$, nCfCHT$_{405}$, nCfCHT$_{351}$, nCfCHT$_{1677}$, nCfCHT$_{276}$, and/or nCfCHT$_{115}$, or by an allelic variant of any of these nucleic acid molecules.

Preferred flea chitinase proteins of the present invention can be used to develop inhibitors that, when administered to an animal, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target includes any flea that produces a protein that can be targeted by an inhibitory compound that inhibits flea chitinase function (e.g., a compound that inhibits flea chitinase, thereby blocking flea development and/or digestive pathways), thereby resulting in the decreased ability of the parasite to cause disease in an animal.

One embodiment of a flea chitinase protein of the present invention is a fusion protein that includes a flea chitinase protein-containing domain attached to one or more fusion segments. Suitable fusion segments for use with the present invention include, but are not limited to, segments that can: enhance a protein's stability; act as an immunopotentiator to enhance an immune response against a flea chitinase protein; and/or assist in purification of a flea chitinase protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea chitinase-containing domain of the protein and can be susceptible to cleavage in order to enable straight-forward recovery of a flea chitinase protein. Fusion proteins are preferably produced by culturing a recombinant cell transformed with a fusion nucleic acid molecule that encodes a protein including the fusion segment attached to either the carboxyl and/or amino terminal end of a chitinase-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. One embodiment of a fusion protein is a chimera of flea chitinase with a functional moiety. This moiety can, for example, have the function of allowing oligomerization of the chimeric chitinase proteins.

The present invention also includes mimetopes of flea chitinase proteins of the present invention. As used herein, a mimetope of a flea chitinase protein of the present invention refers to any compound that is able to mimic the activity of such an chitinase protein, often because the mimetope has a structure that mimics the particular chitinase protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea chitinase nucleic acid molecule. A nucleic acid molecule of the present invention can include an isolated natural flea chitinase gene, cDNA, or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea chitinase nucleic acid molecules of the present invention, or homologs thereof, can be isolated from a natural source or produced using recombinant DNA technology (e.g., polymerase chain reaction (PCR) amplification or cloning) or chemical synthesis. Isolated flea chitinase nucleic acid molecules, and homologs thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a flea chitinase protein of the present invention.

A flea chitinase nucleic acid molecule homolog can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with flea chitinase nucleic acid molecules or by screening the function of a protein encoded by the nucleic acid molecule, e.g., ability to elicit an immune response against at least one epitope of a flea chitinase protein or to effect chitinase activity.

An isolated nucleic acid molecule of the present invention can include a nucleic acid sequence that encodes at least one flea chitinase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea chitinase protein.

A preferred nucleic acid molecule of the present invention, when administered to an animal, is capable of protecting that animal from flea infestation. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an chitinase protein of the present invention), the nucleic acid molecule being delivered to the animal, for example, by direct injection (i.e., as a nucleic acid vaccine) or in a vehicle such as a recombinant virus vaccine or a recombinant cell vaccine.

In one embodiment of the present invention, a preferred flea chitinase nucleic acid molecule includes an isolated nucleic acid molecule that can be any of the following: (a) a nucleic acid molecule comprising SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27; and/or (b) a nucleic acid molecule comprising an at least 18 consecutive nucleotide portion identical in sequence to a consecutive 18 nucleotide portion of a sequence as set forth in (a). A nucleotide comprising an at least 18 consecutive nucleotide portion identical in sequence to a consecutive 18 nucleotide portion of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27 refers to an 18-nucleotide in length nucleic acid molecule that is identical in sequence to an 18-nucleotide portion of one of the named sequences above, as well as to nucleic acid molecules that have nucleotides that extend from both or either of the 5' or 3' end(s) of the consecutive identical 18 nucleotide portion. The 5' and/or 3' extensions can include one or more extensions that have no identity to a flea chitinase nucleic acid molecule of the present invention, as well as extensions that show similarity or identity to cited nucleic acid sequences or portions thereof.

A preferred flea chitinase nucleic acid molecule of the present invention is a nucleic acid molecule comprising apparently full-length chitinase protein coding regions, e.g., nucleic acid molecules encoding an apparently full-length chitinase protein or a post-translationally modified version thereof. Also preferred is a nucleic acid molecule that encodes a flea chitinase protein and/or chitin binding domain that includes the endochitinase domain. In another embodiment, a preferred chitinase nucleic acid molecule of the present invention comprises at least about 18 nucleotides, at least about 20 nucleotides, at least about 30 nucleotides, at least about 40 nucleotides, at least about 100 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1100 nucleotides, at least about 1200 nucleotides, at least about 1300 nucleotides, at least about 1400 nucleotides, at least about 1500 nucleotides, at least about 1600 nucleotides, at least about 1700 nucleotides, and more preferably at least about 1677 or 1749 nucleotides in length.

In one embodiment of the present invention, a preferred flea chitinase nucleic acid molecule includes an isolated nucleic acid molecule which hybridizes under conditions which preferably allow about 30% or less base pair mismatch, more preferably under conditions which allow about 25% or less base pair mismatch, more preferably under conditions which allow about 20% or less base pair mismatch, more preferably under conditions which allow about 15% or less base pair mismatch, more preferably under conditions which allow about 10% or less base pair mismatch and even more preferably under conditions which allow about 5% or less base pair mismatch with a nucleic acid molecule selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and SEQ ID NO:27.

Another embodiment of the present invention includes a nucleic acid molecule that hybridizes in a solution comprising 1×SSC and 0% formamide, at a temperature of about 47.5° C., to a nucleic acid molecule selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27.

Additional preferred flea chitinase nucleic acid molecules of the present invention include nucleic acid molecules comprising a nucleic acid sequence that is preferably at least about 70%, more preferably at least about 75%, more preferably at least about 80% more preferably at least about 85%, more preferably at least about 90%, and even more preferably at least about 95% identical to at least one of the following nucleic acid sequences: SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27. Also preferred are oligonucleotides of any of such nucleic acid molecules. Percent identity may be determined using the program GCG Version 9.0-UNIX using default parameters.

One embodiment of the present invention is a nucleic acid molecule comprising all or part of nucleic acid molecules $nCfCHT_{2610}$, $nCfCHT_{1749}$, $nCfCHT_{405}$, $nCfCHT_{351}$, $nCfCHT_{1677}$, $nCfCHT_{276}$, and/or $nCfCHT_{115}$, or allelic variants of these nucleic acid molecules. As such, preferred nucleic acid molecule of the present invention includes at least a portion of nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:25, and/or SEQ ID NO:27. Also preferred are allelic variants of nucleic acid molecules having these nucleic acid sequences and other homologs of nucleic acid molecules having these nucleic acid sequences; preferably such a homolog encodes or is complementary to a nucleic acid molecule that encodes at least one epitope that elicits an immune response against a protein having an amino acid sequence SEQ ID NO:2, SEQ ID NO:5, SEQ ID NO:8, SEQ ID NO:11, SEQ ID NO:14, SEQ ID NO:17, and/or SEQ ID NO:26. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In another embodiment, a chitinase nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:2, SEQ ID NO:5, SEQ ID NO:8, SEQ ID NO:11, SEQ ID NO:14, SEQ ID NO:17, and/or SEQ ID NO:26. The present invention also includes a chitinase nucleic acid molecule encoding a protein having at least a portion (i.e. fragment) of SEQ ID NO:2, SEQ ID NO:5, SEQ ID NO:8, SEQ ID NO:11, SEQ ID NO:14, SEQ ID NO:17, and/or SEQ ID NO:26, such that the protein has chitinase activity, as well as allelic variants of a chitinase nucleic acid molecule encoding a protein having these sequences, including nucleic acid molecules that have been modified to accommodate codon usage properties of the cells in which such nucleic acid molecules are to be expressed.

In another embodiment, a preferred flea chitinase nucleic acid molecule encodes a chitinase protein comprising at least about 25 amino acids, or at least about 40 amino acids, or at least about 60 amino acids, or at least about 100 amino acids, or at least about 150 amino acids, or at least about 200 amino acids, or at least about 250 amino acids, or at least about 300 amino acids, or at least about 350 amino acids, or at least about 400 amino acids, or at least about 450 amino acids, or at least about 500 amino acids, or at least about 550 amino acids, or at least about 559 or 583 amino acids in length.

In another embodiment, a preferred flea chitinase nucleic acid molecule of the present invention comprises an apparently full-length chitinase coding region, i.e., the preferred nucleic acid molecule encodes an apparently full-length chitinase protein or mature protein thereof.

Knowing the nucleic acid sequences of certain flea chitinase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea chitinase nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate: libraries or DNA using oligonucleotide primers of the present invention. Preferred libraries to screen or from which to amplify nucleic acid molecules include flea $3^{rd}$ instar larvae, wandering larvae, prepupal larvae, and pupae cDNA libraries as well as genomic DNA libraries. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. felis* chitinase nucleic acid molecules or other flea chitinase nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of from about 100 to about 200 nucleotides. The present invention includes oligonucleotides that can be used as, for example, probes to identify nucleic acid molecules, primers to produce nucleic acid molecules, or therapeutic reagents to inhibit flea chitinase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea chitinase nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCfCHT_{2610}$, $nCfCHT_{1749}$, $nCfCHT_{405}$, $nCfCHT_{351}$, $nCfCHT_{1677}$, $nCfCHT_{276}$, and $nCfCHT_{115}$.

Recombinant molecules of the present invention may also (a) contain secretory signals (i.e., signal segment nucleic acid sequences) to enable an expressed flea protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/ or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include *C. felis* chitinase nucleic acid molecules disclosed herein. Particularly preferred nucleic acid molecules with which to transform a cell include $nCfCHT_{2610}$, $nCfCHT_{1749}$, $nCfCHT_{405}$, $nCfCHT_{351}$, $nCfCHT_{1677}$, $nCfCHT_{276}$, and $nCfCHT_{115}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea chitinase proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include Salmonella, Escherichia, Bacillus, Caulobacter, Listeria, Saccharomyces, Pichia, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_\chi$3987 and SR-11 $_\chi$4072; Caulobacter; Pichia; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea chitinase nucleic acid molecules encoding one or more proteins of the present invention and one or more other nucleic acid molecules encoding other protective compounds, as disclosed herein, e.g., to produce multivalent vaccines.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications.

Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea chitinase proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a flea chitinase protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea chitinase protein of the present invention or a mimetope thereof (e.g., anti-*C. felis* chitinase antibodies). As used herein, the term, selectively binds to a chitinase protein, refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-chitinase antibody of the present invention preferably selectively binds to a flea chitinase protein respectively in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce chitinase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal susceptible to flea infestation, is capable of protecting that animal from flea infestation. Therapeutic compositions of the present invention include at least one of the following protective molecules: an isolated flea chitinase protein; a mimetope of an isolated flea chitinase protein; an isolated flea chitinase nucleic acid molecule; and/or a compound derived from said isolated flea chitinase protein that inhibits chitinase activity. Chitinase activity includes binding to a chitin molecule and/or hydrolyzing a chitin molecule. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea infestation. Preferred fleas to target are heretofore disclosed. One example of a protective molecule is a vaccine, such as, but not limited to, a naked nucleic acid vaccine, a recombinant virus vaccine, a recombinant cell vaccine, and a recombinant protein vaccine. Another example of a protective molecule is a compound that inhibits chitinase activity, such as an isolated antibody that selectively binds to a flea chitinase protein, a substrate analog of a flea chitinase, anti-sense-, triplex formation-, ribozyme-, and/or RNA drug-based compounds, or other inorganic or organic molecules that inhibit chitinase activity. Inhibiting flea chitinase activity can refer to the ability of a compound to reduce the activity of flea chitinase. Inhibiting flea chitinase activity can also refer to the ability of a compound to reduce the amount of flea chitinase in a flea.

Another embodiment of the present invention includes a method to reduce a flea infestation in an animal susceptible to flea infestation. Such a method includes the step of administering to the animal a therapeutic molecule comprising a protective compound selected from the group consisting of (a) an isolated flea chitinase protein; (b) a mimetope of an isolated flea chitinase protein; (c) an isolated flea chitinase nucleic acid molecule; and (d) a compound derived from an isolated flea chitinase protein that inhibits chitinase activity.

Therapeutic compositions of the present invention can be administered to any animal susceptible to flea infestation, preferably to mammals, and more preferably to dogs, cats, humans, ferrets, horses, cattle, sheep, and other pets, economic food animals, work animals and/or zoo animals. Preferred animals to protect against flea infestation include dogs, cats, humans, and ferrets, with dogs and cats being particularly preferred.

As used herein, the term derived, or the term derived from, refers to a peptide, antibody, mimetope, nucleic acid molecule, or other compound that was obtained from a flea chitinase protein or nucleic acid molecule of the present invention. Methods to obtain derivatives from a chitinase molecule of the present invention are known in the art, and as such include, but are not limited to molecular modeling of chitinase to determine active sites, i.e. sites that interact with other molecules, such as chitin, and predicting from these active sites smaller fragments and/or mimetopes that retain and/or mimic these active sites, thereby inhibiting chitinase activity; screening of peptide or small chemical compound libraries against chitinase proteins of the present invention; and screening of polyclonal or monoclonal antibodies to find antibodies that specifically bind chitinase proteins of the present invention.

A chitinase inhibitor of the present invention is identified by its ability to bind to, modify, or otherwise interact with, a flea chitinase protein, thereby inhibiting the activity of chitinase. Suitable inhibitors of chitinase activity are compounds that inhibit chitinase protein activity in at least one of a variety of ways: (a) by binding to or otherwise interacting with or otherwise modifying the chitin binding i.e. ligand binding site; (b) by binding to or otherwise interacting with or otherwise modifying the chitinase active site, i.e. the active site residues of the chitinase protein that are directly involved breaking down chitin; (c) by binding to the chitinase protein and thus reducing the availability of the chitinase in solution; and (d) by interacting with other regions of the chitinase protein to inhibit chitinase activity, for example, by allosteric interaction.

Flea chitinase inhibitors can be used directly as compounds in compositions of the present invention to treat animals as long as such compounds are not harmful to host animals being treated. Preferred chitinase inhibitors of the present invention include, but are not limited to, flea chitinase substrate analogs, and other molecules that bind to a flea chitinase (e.g., to an allosteric site) in such a manner that chitinase activity of the flea chitinase is inhibited. A chitinase substrate analog refers to a compound that interacts with (e.g., binds to, associates with, modifies) the active site of an chitinase protein. A preferred chitinase substrate analog inhibits chitinase activity. Chitinase substrate analogs can be of any inorganic or organic composition. Chitinase substrate analogs can be, but need not be, structurally similar to a chitinase natural substrate as long as they can interact with the active site of that chitinase protein. Chitinase substrate analogs can be designed using computer-generated structures of chitinase proteins of the present invention or computer structures of chitinase's natural substrates. Preferred sites to model include one or more of the active sites of chitinase proteins. Substrate analogs can also be obtained by generating random samples of molecules, such as oligonucleotides, peptides, peptidomimetic compounds, or other inorganic or organic molecules, and screening such samples for their ability to interfere with interaction between chitin and chitinase, e.g. by affinity chromatography techniques. A preferred chitinase substrate analog is a chitinase mimetic compound, i.e., a compound that is structurally and/or functionally similar to a natural substrate of an chitinase of the present invention, particularly to the region of the substrate that interacts with the chitinase active site, but that inhibits chitinase activity upon interacting with the chitinase active site.

The present invention also includes a therapeutic composition comprising at least one protective molecule of the present invention in combination with at least one additional compound protective against one or more infectious agents.

In one embodiment, a therapeutic composition of the present invention can be used to protect an animal from flea infestation by administering such composition to a flea in order to prevent infestation. Such administration to the flea and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present on the surface of or in the blood of a host animal that has been administered a therapeutic composition of the present invention.

In accordance with the present invention, a host animal (i.e., an animal that is or is capable of being infested with fleas) is treated by administering to the animal a therapeutic composition of the present invention in such a manner that the composition itself (e.g., a chitinase inhibitor, a chitinase synthesis suppressor (i.e., a compound that decreases the production or half-life of chitinase in fleas), a chitinase mimetope, or a anti-chitinase or antibody) or a product generated by the animal in response to administration of the composition (e.g., antibodies produced in response to administration of a flea chitinase protein or nucleic acid molecule, or conversion of an inactive inhibitor "prodrug" to an active chitinase inhibitor) ultimately enters the flea. A host animal is preferably treated in such a way that the compound or product thereof is present on the body surface of the animal or enters the blood stream of the animal. Fleas are then exposed to the composition or product when they feed from the animal. For example, flea chitinase inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing chitinase activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal, (g) altering the development of flea larvae (e.g., by decreasing feeding behavior, inhibiting growth, inhibiting (e.g., slowing or blocking) molting, and/or otherwise inhibiting maturation to adults), and/or (h) altering or decreasing the ability of fleas or flea larvae to digest a blood meal.

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation. For example, proteins, mimetopes thereof, and antibodies thereof can be used as immunotherapeutic agents.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from flea infestation. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition, including a recombinant protein vaccine, is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times, on a daily, weekly, monthly or yearly regimen; routes of administration can be determined by one skilled in the art, and may include any route. A preferred route of administration of an inhibitory compound when administering to fleas is a topical, or "spot-on" formulation administered to the body surface of the animal, so that a flea would encounter the inhibitory compound when attached to the animal; another preferred route of administration of an inhibitory compound is an oral formulation that, when fed to an animal, would enter the bloodstream of the animal, which would then be transferred to a flea while feeding from the animal.

A recombinant protein vaccine of the present invention comprises a recombinantly-produced flea chitinase protein of the present invention that is administered to an animal according to a protocol that results in the animal producing a sufficient immune response to protect itself from a flea infestation. Such protocols can be determined by those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome, i.e., a viral vector. Preferred viral vectors include those based on alphaviruses, poxviruses, adenoviruses, herpesviruses, picornaviruses, and retroviruses, with those based on alphaviruses, such as sindbis or Semliki forest virus, species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, conjunctival, intraocular, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in U.S. Pat. No. 5,766,602 to Xiong and Grieve, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising a flea chitinase nucleic acid molecule of the present invention is administered according to a protocol that results in the animal producing a sufficient immune response to protect itself from flea infestation. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal, intraocular, conjunctival, and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

One therapeutic composition of the present invention includes an inhibitor of flea chitinase activity, i.e., a compound capable of substantially interfering with the function of a flea chitinase susceptible to inhibition by an inhibitor of flea chitinase activity. An inhibitor of chitinase activity can be identified using flea chitinase proteins of the present invention. An inhibitor of chitinase function can be identified using flea chitinase proteins of the present invention. A preferred inhibitor of chitinase function is a compound capable of substantially interfering with the function of a flea chitinase protein and which does not substantially interfere with host animal proteins. As used herein, a compound that does not substantially inhibit or interfere with host animal proteins is one that, when administered to a host animal, the host animal shows no significant adverse effects attributable to the compound and which, when administered to an animal in an effective manner, is capable of protecting that animal from flea infestation.

One embodiment of the present invention is a method to identify a compound capable of inhibiting chitinase activity of a flea. Such a method includes the steps of (a) contacting (e.g., combining, mixing) an isolated flea chitinase protein, preferably a *C. felis* chitinase protein of the present invention, with a putative inhibitory compound under conditions in which, in the absence of the compound, the protein has chitinase activity, and (b) determining if the putative inhibitory compound inhibits the activity. Chitinase activity can be determined in a variety of ways known in the art, including but not limited to determining the ability of chitinase to bind to or otherwise interact with chitin and/or hydrolyze chitin into chitobiose. Such conditions under which a chitinase protein has chitinase activity include conditions in which a chitinase has a correct three-dimensionally folded structure under physiologic conditions, i.e. physiologic pH, physiologic ionic concentrations, and physiologic temperatures.

Putative inhibitory compounds to screen include antibodies (including fragments and mimetopes thereof), putative substrate analogs, and other, preferably small, organic or inorganic molecules. Methods to determine chitinase activity are known to those skilled in the art; see, for example, the Examples section of the present application. Methods to determine binding of a putative inhibitory compound to a chitinase protein of the present invention are known to those of skill in the art and include, for example, determining changes in molecular mass using surface plasmon resonance (e.g., determining light scatter by an inhibitor of a chitinase protein, before and after contacting the inhibitor or protein with a chitinase protein or inhibitor, respectively) or screening for compounds that inhibit interaction between chitin and chitinase.

A preferred method to identify a compound capable of inhibiting chitinase activity includes contacting an isolated flea chitinase protein having an amino acid sequence selected from the group consisting of: (a) a protein comprising an amino acid sequence selected from the group consisting of SEQ ID NO:2, SEQ ID NO:5, SEQ ID NO:8, SEQ ID NO:11, SEQ ID NO:14, SEQ ID NO:17, and SEQ ID NO:26; (b) a protein comprising an at least 25 consecutive amino acid portion identical in sequence to a consecutive amino acid portion of a sequence as set forth in (a), wherein the protein has chitinase activity; (c) a protein comprising a fragment of a protein as set forth in (a), wherein the fragment has an activity selected from the group consisting of binding to a chitin molecule and hydrolyzing a chitin molecule; and (d) a protein encoded by an allelic variant of a nucleic acid molecule that encodes any protein of (a), (b), or (c), with a putative inhibitory compound under conditions in which, in the absence of the compound, the protein has chitinase activity; and determining if the putative inhibitory compound inhibits the activity.

Another embodiment of the present invention is an assay kit to identify an inhibitor of a flea chitinase of the present invention. This kit comprises an isolated flea chitinase of the present invention, and a means for determining inhibition of an activity of flea chitinase, where the means enables detection of inhibition. Detection of inhibition of flea chitinase identifies a putative inhibitor to be an inhibitor of flea chitinase. Means for determining inhibition of flea chitinase include an assay system that detects binding of a putative inhibitor to a flea chitinase molecule, and an assay system that detects interference by a putative inhibitor of the ability of flea chitinase to hydrolyze a chitin molecule. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This example describes the cloning and sequencing of flea chitinase (CHT) nucleic acid molecules from the flea *Ctenocephalides felis*.

Degenerate primers were designed based on several conserved regions of published chitinase amino acid sequences from *Anopheles gambiae, Drosophila melanogaster, Aedes aegypti, Manduca sexta* and *Bombyx mori*. Insect chitinases belong to the family 18-glycosylhydrolases, which have two regions of conserved amino acids in their catalytic domain. Three degenerate primers, designed based on conserved regions of various conserved regions of various insect chitinase sequences, were used in a nested PCR as follows. Vector sense primer, SK-1, having a nucleotide sequence 5' CGC TCT AGA ACT AGT GGA TC 3', denoted SEQ ID NO:39, was used in combination with reverse primer bchitinase2R, having a nucleotide sequence 5' RTC CAT RTC WAT WGC CCA 3', (wherein R represents A or G, W represents A or T), denoted SEQ ID NO:40, in a first PCR reaction using the mixed instar larval *C. felis* cDNA library and the prepupal *C. felis* cDNA library, prepared as described in Silver, et al. U.S. Ser. No. 08/747,221, filed Nov. 12, 1996, as the templates. The products of the first reactions (8 μl) were used as the templates for second nested PCR reactions using reverse primer chitcatIIreg-deg-R, having a nucleotide sequence 5' GCW GCN CCN GGR TAY TCC CA 3', wherein Y represents C or T, N represents A or C or G or T, designated SEQ ID NO:19, and forward primer chitcatIreg-deg-F, having the nucleotide sequence 5' ATG RTN GCW GTW GGW GGW TGG CG 3', denoted SEQ ID NO:20.

A DNA fragment of about 115 nucleotides, referred to herein as $nCfCHT_{115}$, was isolated from each of the second PCR reactions from the mixed instar larval and prepual libraries. The DNA fragments were purified using a Gel Purification Kit, available from Qiagen, Chatsworth, Calif., and combined. The purified fragment was ligated into the pCRII™ TA cloning vector, available from Invitrogen, and sequenced using standard sequence methods. The sequence of $nCfCHT_{115}$, the coding strand of which has nucleic acid sequence SEQ ID NO:16 and the complementary strand of which has nucleic acid sequence SEQ ID NO:18, revealed that $nCfCHT_{115}$ encoded a partial length protein, denoted SEQ ID NO:17, also known as $PCfCHT_{38}$, assuming a first codon spanning from nucleotide 2 to nucleotide 4 of SEQ ID NO:16, having homology with other insect chitinases.

The nucleic acid molecule $nCfCHT_{115}$, was labeled with $^{32}$P-ATP using the MEGAPRIME™ labeling kit, (available from Amersham, Piscataway, N.J.) and used as a probe to screen approximately $5 \times 10^5$ plaques from the flea mixed instar cDNA library. Filters were hybridized with the radiolabeled probe in the following buffer: 5×SSC (for recipe see Sambrook, et al. ibid.), 0.5% sodium dodecyl sulfate (SDS) (available from Sigma, St. Louis, Mo.), 0.1% salmon sperm DNA (available from Sigma) and 5×Denhardt's reagent (for recipe see Sambrook, et al., ibid.) for about 14 hours at 45° C. The filters were then washed one time per wash, in three washes with the following buffers in sequence: buffer 1, 5×SSC, 1% SDS; buffer 2, 2×SSC, 0.5% SDS; and buffer 3, 1×SSC, 0.1% SDS. All washes were done for about 30 minutes at 55° C. One positive phage plug was generated. Subsequent plaque purification, using standard techniques, conversion to double stranded plasmid DNA using EXASSIST™ (available from Stratagene), and DNA sequencing revealed the isolation of a putative 5' truncated flea chitinase of 2610 nucleotides denoted herein as $nCfCHT_{2610}$, which has the coding strand SEQ ID NO:1 and the complementary strand SEQ ID NO:3. As mentioned previously, SEQ ID NO:1 appears to be truncated at the 5' end, since it lacks a start codon. SEQ ID NO:1 encodes a protein of 583 amino acids, denoted $PCfCHT_{583}$, the sequence of which is represented herein as SEQ ID NO:2. $PCfCHT_{583}$ has a calculated molecular weight of 66 kilodaltons and a calculated isoelectric point of 6.1. The nucleic acid sequence encoding SEQ ID NO:2 is $nCfCHT_{1749}$, which has the coding strand SEQ ID NO:4 and the complementary strand SEQ ID NO:6. SEQ ID NO:5 represents the same amino acid sequence represented by SEQ ID NO:2. Nucleic acid $nCfCHT_{1677}$, represented herein as SEQ ID NO:13, the coding strand, and SEQ ID NO:15, the complement strand, represents a nucleic acid encoding a mature chitinase protein, i.e. a chitinase protein lacking a signal sequence. This protein is denoted as $PCfCHT_{559}$, which is represented by SEQ ID NO:14.

To obtain a nucleic acid molecule including more of the 5' portion of the C. felis chitinase cDNA, 5' RACE (Rapid Ampification of cDNA ends) cloning, using the MARATHON™ cDNA kit (available from Clontech, Palo Alto, Calif.) according to the manufacturer's protocol, was performed on RNA extracted from prepupal flea larvae, using standard procedures. The 5' RACE cloning utilized a nested PCR reaction with ADVANTAGE™ cDNA polymerase (available from Clontech) and was performed as follows: the initial PCR used a primer denoted chit5'RACE670r having the sequence 5'-AGCAAACCCT GCCCAATTTC C-3', i.e. SEQ ID NO:21, in combination with a primer corresponding to a sequence ligated to the 5' end of the cDNA pool denoted AP1, having the sequence 5'-CCATCCTAAT ACGACTCACT ATAGGGC-3', i.e. SEQ ID NO:22, with a flea prepupal cDNA RACE pool as the template using the following PCR amplification conditions: (a) one cycle at 95° C. for 1 minute; then (b) 5 cycles of 94° C. for 10 seconds, 62° C. for 30 seconds, 72° for 45 seconds; then (c) 10 cycles of 94° C. for 10 seconds, 59° C. for 30 seconds, 72° C. for 45 seconds; then (d) 20 cycles of 94° C. for 10 seconds, 56° C. for 30 seconds, 72° C. for 45 seconds. Reaction products of this PCR amplification were used as the template in the nested PCR using a primer denoted chit5'326R 5'-TTTTTCCGCC TTCAGCCCAT C-3', having the nucleic acid sequence SEQ ID NO:23 in combination with a primer denoted AP2, having the sequence 5'-ACTCACTATA GGGCTCGAGC GGC-3', i.e. SEQ ID NO:24, under the following conditions: (a) one cycle at 95° C. for 1 minute; then (b) 5 cycles of 94° C. for 10 seconds, 61° C. for 30 seconds, 72° C. for 30 seconds; then (c) 10 cycles of 94° C. for 10 seconds, 59° C. for 30 seconds, 72° C. for 30 seconds; then (d) 15 cycles of 94° C. for 10 seconds, 57° C. for 30 seconds, 72° C. for 30 seconds.

An approximately 400-base pair band was excised from a gel containing this PCR reaction, purified using the QIAQUICK™ column (available from Qiagen, Chatsworth, Calif.), and T/A cloned using the TOPO T/A™ cloning kit, (available from Invitrogen, Carlsbad, Calif.). The purified product, denoted $nCfCHT_{405}$, which contained 405 base pairs includes a coding strand denoted SEQ ID NO:7, and a complementary sequence denoted SEQ ID NO:9. Sequence analysis of this purified product revealed the 5' end corresponding to $nCfCHT_{2610}$, indicating that $nCfCHT_{2610}$ was missing only the initiating codon at its 5' terminus. Sequence analysis of SEQ ID NO:7 indicates that $nCfCHT_{405}$, encodes a protein denoted $PCfCHT_{117}$, having the sequence represented by SEQ ID NO:8. The nucleic acid molecule encoding the open reading frame for $PCfCHT_{117}$, also denoted SEQ ID NO:11, is $nCfCHT_{351}$, represented by SEQ ID NO:10, (coding strand) SEQ ID NO:12 (complementary strand). The protein $PCfCHT_{92}$, represented by SEQ ID NO:26, represents the mature protein, i.e. lacking a signal sequence, corresponding to $PCfCHT_{117}$. SEQ ID NO:26 is encoded by $nCfCHT_{276}$, represented by SEQ ID NO:25, (coding strand) and SEQ ID NO:27, (complementary strand).

SEQ ID NO:1 and SEQ ID NO:7, the coding strands of $nCfCHT_{2610}$ and $nCfCHT_{405}$, respectively, together encode a complete flea chitinase nucleic acid molecule, containing 5' and 3' untranslated regions, a start codon, and a stop codon. $nCfCHT_{2610}$ and $nCfCHT_{405}$ share a common stretch of nucleotide sequence, spanning from nucleotide 1 to nucleotide 348 of $nCfCHT_{2610}$ and spanning from nucleotide 58 to nucleotide 405 of $nCfCHT_{405}$. Nucleotide changes in this common stretch, likely due to allelic variations in the cDNAs or multiple gene copies, consist of the following changes in $nCfCHT_{2610}$ relative to $nCfCHT_{405}$: nucleotide 39, C to A; nucleotide 69, T to A; nucleotide 150, A to G; nucleotide 237, G to A; nucleotide 264, T to C; nucleotide 279, C to T; nucleotide 289, G to A; nucleotide 290, C to T; nucleotide 291, C to T; and nucleotide 303, T to G. The only nucleotide changes resulting in an amino acid change occur at nucleotide 289 and nucleotide 290, the change at nucleotide 291 being silent, from GCC to ATT, which results in a change to an isoleucine residue from an alanine residue.

Comparison of nucleic acid SEQ ID NO:1 with nucleic acid sequences reported in GenBank indicates that SEQ ID NO:1 shared the most similarity with an *Aedes aegypti* (yellow fever mosquito) chitinase cDNA (GenBank accession number AF026491). Comparison of SEQ ID NO:4, the coding region of SEQ ID NO:1, showed 62% identity with the *Aedes aegypti* chitinase cDNA. Comparison of amino acid sequence SEQ ID NO:2 with amino acid sequences reported in GenBank indicates that SEQ ID NO:2 showed the most similarity, i.e. about 64%, with the *Manduca sexta* endochitinase precursor chitinase polypeptide (GenBank accession number 544013). Sequence analysis was performed using the GCG GAP program as described above.

A partial-length predicted chitinase protein, referred to herein as PCfCHT$_{489}$ was expressed as a recombinant fusion tagged protein as follows. A nucleic acid molecule encoding PCfCHT$_{489}$, referred to herein as nCfCHT$_{1478}$ comprising nucleotides 320 through 1650 of SEQ ID NO:1, and sequence added by the primers and vector as described below, was constructed as follows. A PCR was performed using SEQ ID NO:1 as template with sense primer ChitEXPforfragBAM, having a nucleic acid sequence 5' AAG GAT CCG GTG AAA TTA CAA ATA GCC G 3', denoted herein as SEQ ID NO:34 and having a BamH1 site shown in bold, in conjunction with antisense primer ChitEXPrev2fragXhoI, having a nucleic acid sequence 5' TTC TCG AGT TAT AAG TCT CGA CAT CTT TC 3', designated herein as SEQ ID NO:35 and having an XhoI site shown in bold, under the following amplification conditions: (a) one cycle at 95° C. for one minute; (b) thirty cycles at 94° C. for ten seconds, 50° C. for fifteen seconds, and 70° C. for one minute forty-five seconds; in reactions containing 0.2 mM dNTPs, 0.5 uM of each primer, one uL of KlenTaq polymerase, 1 uL of ~0.5 ug/mL template and 5 uL of 10×KlenTaq polymerase buffer. This PCR reaction created a PCR product having primer-added sequence in addition to template sequence with the primer-added sequence corresponding to nucleotides 91 to 118 and nucleotides 1450 to 1478 of nCfCHT$_{1478}$. The resulting PCR product was digested with BamH1 and Xho1 restriction enzymes and ligated into λcro plasmid vector, the production of which is described in U.S. Pat. No. 5,569,603 by Tripp et al., issued Oct. 29, 1996, that had been digested with BamH1 and Xho1 and gel purified, producing recombinant molecule pλcro-nCfCHT$_{1478}$. This ligation created a product having vector sequence in addition to template sequence and primer sequence with the vector-added fusion tag sequence corresponding to nucleotides 1 to 90 of nCfCHT$_{1478}$. Nucleic acid molecule nCfCHT$_{1478}$ is represented herein by a coding strand having nucleic acid sequence SEQ ID NO:28 and a complementary strand having nucleic acid sequence SEQ ID NO:30. Translation of SEQ ID NO:28 indicates that nucleic acid molecule nCfCHT$_{1478}$ encodes protein PCfCHT$_{489}$, represented herein as SEQ ID NO:29, assuming a start codon at nucleotides 1 through 3 of SEQ ID NO:28 and a stop codon at nucleotides 1468 through 1470 of SEQ ID NO:28. The resulting recombinant molecule was transformed into *E. coli* strain BL-21 available from Novagen Inc., Madison, Wis., to form recombinant cell BL-21-pλcro-nCfCHT$_{1478}$. The recombinant cell was grown under standard conditions at 32° C. and production of protein was induced by shifting the temperature to 42° C. and incubating for an additional 2–3 hours. Expression of protein was confirmed using Coomasie-blue stained Tris-glycine gel and Western blot using a T7 tag antibody which showed expression of an about 66 kDa protein.

*E. coli* cells expressing PCfCHT$_{489}$ were harvested from about 4 liters of media by centrifugation and re-suspended in about 120 ml of Solubilization Buffer made of 50 mM Tris, pH 8, 50 mM NaCl, 1 mM phenylmethylsulfonylfluoride (PMSF). The cells were broken using a Parr bomb, available from Parr Instrument Co., Moline, Ill., at 2000 psi for 20 minutes and the sample was centrifuged at about 20,000×g for 30 min at 4° C. The supernatant (S1) was recovered and the pellet was resuspended in about 60 ml of Solubilization Buffer and centrifuged at about 20,000×g for 30 min at 4° C. The supernatant (S2) was recovered and the pellet was resuspended in about 120 ml Solubilization Buffer with 0.1% Triton X-100 and centrifuged at about 20,000×g for 30 min at 4° C. The supernatant (S3) was recovered and the pellet was resuspended in about 120 ml Solubilization Buffer supplemented with 8M urea and 1 mM DTT, rocked overnight at room temperature, and centrifuged at about 20,000×g for 30 min at 15° C. The supernatant (S4) was recovered and the pellet (P4) was resuspended in about 60 ml Solubilization Buffer supplemented with 8M urea and 1 mM DTT. Aliquots of the four supernatants, i.e. S1–S4, and the final pellet were assayed for the presence of PCfCHT$_{489}$ by immunoblot using a T7 tag monoclonal antibody, available from Novagen, Inc. Madison, Wis. The results indicated that the majority of the PCfCHT$_{489}$, which ran at about 66 kDa on the electrophoresis gel, was located in the S4 supernatant. The PCfCHT$_{489}$ in the S4 supernatant was loaded onto a 5.0 ml, Metal chelating HiTrap™ column charged with NiCl$_2$, available from Amersham Pharmacia Biotech Inc., Piscataway, N.J., previously equilibrated with Buffer A, made of 50 mM Tris 8.0, 50 mM NaCl, 10 mM Imidazole, and 8M urea. The column was washed with Buffer A until all unbound protein was removed. Bound PCfCHT$_{489}$ was eluted with a linear gradient from 10 mM to 1 M imidazole in Buffer A. Column fractions were analyzed for the presence of PCfCHT$_{489}$ by immunoblot using a T7 tag monoclonal antibody. The results indicated that the PCfCHT$_{489}$ was eluted at about 200 mM imidazole. This preparation yielded approximately 2.6 mg of purified PCfCHT$_{489}$.

The purified PCfCHT$_{489}$ was used to produce an anti-PCfCHT$_{489}$ polyclonal antiserum as follows. A rabbit was immunized with PCfCHT$_{489}$ that was diluted to about 0.1 mg/ml in PBS. About 0.5 milliliter of the dilution was mixed 1:1 with Complete Freund's Adjuvant. In the primary immunization, about 500 μl was injected subcutaneously into 5 different regions (0.1 ml/site) and 500 μl was injected intradermally into 5 different sites (0.1 ml/site). Boosts were administered with Incomplete Freund's Adjuvant and were given on days 15, 36, and 134 in 250 μl/site doses intramuscularly in 4 sites. Blood samples were obtained prior to immunization and approximately every two weeks after the primary immunization. Serum samples from the pre-immunization and day 49 after the primary immunization bleeds were used for subsequent immunoblot experiments.

A full-length fusion tagged chitinase protein, referred to herein as PCfCHT$_{635}$ was expressed as follows. A nucleic acid molecule encoding PCfCHT$_{635}$, referred to herein as nCfCHT$_{1919}$ comprising nucleotides 1 through 1727 of SEQ ID NO:1, and sequence added by the primers and vector as described below, was constructed as follows. A PCR reaction was performed using SEQ ID NO:1 as template, using forward primer CHITSELECTHindIIISEN, having a nucleotide sequence 5' TTA AGC TTG AAA TGG GAA GAC ACT GGA ACT TGT TAG 3', having a HindIII site shown in bold and containing an "ATG" codon to initiate translation, designated herein as SEQ ID NO:36, in conjunction with reverse primer CHITSELECTBamH1ANTI+tag: 5' TTG GAT CCC AAT ATA GGT AAG TCA ATA TAT TTC 3', having a BamH1 site shown in bold, designated herein as SEQ ID NO:37 using the following PCR reaction and thermocycling conditions: (1) one cycle at 95° C. for one minute; (2) thirty two cycles at 94° C. for ten seconds, 50° C. for thirty seconds, and 70° C. for two minutes thirty seconds, in reactions containing 0.2 mM dNTPs, 0.5 uM of each primer, one uL of KlenTaq polymerase, 1 uL of ~0.5 ug/mL template and 5 uL of 10×KlenTaq polymerase buffer. This PCR reaction created a PCR product having primer-added sequence in addition to template sequence with the primer-added sequence corresponding to nucleotides 1 to 36 and nucleotides 1739 to 1771 of nCfCHT$_{1919}$. The resulting PCR product was digested with BamH1 and HindIII restriction enzymes and ligated into the vector pIZ/V5-His which had been digested with BamH1 and HindIII to create recombinant molecule pIZ/V5-His-nCfCHT$_{1919}$. This ligation created a product having vector sequence in addition to template sequence and primer sequence with the vector-added sequence corresponding to nucleotides 1772 to 1919 of nCfCHT$_{1919}$. Nucleic acid molecule nCfCHT$_{1919}$ is represented herein by a coding strand having nucleic acid sequence SEQ ID NO:31 and a complementary strand having nucleic acid sequence SEQ ID NO:33. Translation of SEQ ID NO:31 indicates that nucleic acid molecule nCfCHT$_{1919}$ encodes protein PCfCHT$_{635}$, represented herein as SEQ ID NO:32, assuming a start codon at nucleotides 12 through 14 of SEQ ID NO:31 and a stop codon at nucleotides 1917 through 1919 of SEQ ID NO:31. The recombinant molecule was transformed into Top 10 cells, available from Invitrogen, to form recombinant cells T10-pIZ/V5-His-nCfCHT$_{1919}$. Plasmid DNA harvested from T10-pIZ/V5-His-nCfCHT$_{1919}$ cells was used to transfect High Five™ (*Tricuplusia ni*) insect cells, available from Invitrogen, using Cell-Fectin™, available from Gibco BRL, per the manufacturers protocols, to form recombinant cell H5-pIZ/V5-His-nCfCHT$_{1919}$.

Expression of protein from cell culture supernatants was confirmed using Coomasie-blue stained Tris-glycine gel and Western blot using an anti-V5 tag antibody which showed expression of an about 98 kDa protein. The predicted size of the chitinase molecule is approximately 66 kDa, however, analysis of the amino acid sequence of this molecule revealed the presence of multiple O-linked glycosylation epitopes. The postulated addition of carbohydrates at these O-linked glycosylation epitopes by the insect cells could account for the increased molecular mass seen.

About 3.5 liters of supernatant from cultures of High Five™ cells producing PCfCHT$_{635}$ were brought to about 30% saturation with ammonium sulfate and centrifuged at about 12,000×g for about 30 min at 4° C. to pellet the precipitated material. After centrifugation, the pellet was retained and the supernatant was brought to about 90% saturation with ammonium sulfate and centrifuged as before. The pelleted material from both steps were separately resuspended in about 175 ml of Nickel A buffer, made up of 50 mM Tris, pH 8, 10 mM imidazole. The resuspended pellets were assayed for PCfCHT$_{635}$ by immunoblot using an anti-V5 tag monoclonal antibody, available from Invitrogen. The results indicated that the majority of PCfCHT$_{635}$, which ran at about 97 kDa on the electrophoresis gel, was precipitated by adjusting the ammonium sulfate concentration from about 30% saturation to about 90% saturation. The PCfCHT$_{635}$ was loaded, in three aliquots, onto a 5.0 ml, Metal chelating HiTrap™ column charged with NiCl$_2$, available from Amersham Pharmacia Biotech Inc., previously equilibrated with Nickel A buffer. The column was washed with Nickel A buffer until all unbound protein was removed. Bound PCfCHT$_{635}$ was eluted with a linear gradient from 10 MM to 1 M imidazole in Nickel A buffer. The resulting column fractions were supplemented with Complete protease inhibitor cocktail, available from Roche Molecular Biochemicals, Indianapolis, Ind., and analyzed for the presence of PCfCHT$_{635}$ by immunoblot using an anti-V5 tag monoclonal antibody. The results indicated that PCfCHT$_{635}$ was eluted at about 200 mM imidazole.

The fractions containing PCfCHT$_{635}$ were pooled and diafiltered into about 8 ml of Anion A buffer, made up of 50 mM Tris, pH 8.0, 10 mM NaCl, using a Centricon Plus 20 10-kDa concentrator, available from Millipore Corp., Bedford, Mass., in preparation for anion exchange chromatography. The PCfCHT$_{635}$ was loaded onto a BioScale Q2 anion exchange column, available from Bio-Rad, Hercules, Calif., previously equilibrated with Anion A buffer. The column was washed with Anion A buffer until all unbound protein was removed. Protein bound to the column was eluted with a linear gradient from 10 mM to 1 M NaCl in Anion A buffer. The resulting fractions were analyzed for the presence of PCfCHT$_{635}$ by coomassie-stained SDS-PAGE and immunoblot using an anti-V5 tag monoclonal antibody. The results indicated that PCfCHT$_{635}$ was eluted at about 250 mM NaCl, and was about 90% pure.

A full-length untagged chitinase protein, referred to herein as PCfCHTL$_{584}$ was expressed as follows. A nucleic acid molecule comprising nucleotides 1 through 1749 of SEQ ID 1, corresponding to the entire coding region of SEQ ID NO:1, encoding a full-length chitinase molecule, referred to herein as PCfCHTL$_{584}$ was amplified by PCR using SEQ ID NO:1 as template, using sense primer CHITSELECTHindIIISEN, i.e. SEQ ID NO:36 which contains an "ATG" codon to initiate translation, and antisense primer CHITSELECTBamH1ANTIstop: 5' TTG GAT CCT TAC AAT ATA GGT AAG TCA ATA TAT TTC 3' having a BamH1 site shown in bold, designated herein as SEQ ID NO:38, under the following PCR reaction and thermocycling conditions: (1) one cycle at 95° C. for one minute; (2) thirty two cycles at 94° C. for ten seconds, 50° C. for thirty seconds, and 70° C. for two minutes thirty seconds, in reactions containing 0.2 mM dNTPs, 0.5 uM of each primer, one uL of KlenTaq polymerase, 1 uL of ~0.5 ug/mL template and 5 uL of 10×KlenTaq polymerase buffer. The PCR product was digested with BamH1 and HindIII restriction enzymes and ligated into the vector pIZ/V5-His which had been digested with BamH1 and HindIII. The resulting recombinant molecule, referred to herein as pIZ/V5-HisnCfCHTL$_{1752}$ was transformed into Top 10 cells, available from Invitrogen, to form recombinant cells T10-pIZ/V5-HisnCfCHTL$_{1752}$. Plasmid DNA harvested from T10-pIZ/V5-HisnCfCHTL$_{1752}$ cells was used to transfect High Five™ insect cells, available from Invitrogen, using Cell-Fectin™, available from Gibco, BRL per manufacturers protocols to create recombinant cells H5-pIZ/V5-HisnCfCHTL$_{1752}$.

Expression of protein from cell culture supernatants was confirmed using Coomasie-blue stained Tris-glycine gel and Western blot using an anti-PCfCHT$_{489}$ polyclonal antiserum which showed expression of an about 90 kDa protein. The predicted size of the chitinase molecule is approximately 66 kDa, however, analysis of the amino acid sequence of this molecule revealed the presence of multiple O-linked glycosylation epitopes. The postulated addition of carbohydrates at these O-linked glycosylation epitopes by the insect cells could account for the increased molecular mass seen.

About 3.7 liters of supernatant from cultures of High Five™ cells producing PCfCHTL$_{584}$ were brought to about 30% saturation with ammonium sulfate and centrifuged at about 12,000×g for about 30 min at 4° C. to pellet the precipitated material. After centrifugation, the pellet was retained and the supernatant was brought to about 90% saturation with ammonium sulfate and centrifuged as before. The pelleted materials from each step were separately resuspended in about 100 ml of Nickel A buffer. The resuspended pellets were assayed for PCfCHTL$_{584}$ by immunoblot using an anti-PCfCHT$_{489}$ polyclonal antiserum, produced as described above. The results indicated that the majority of PCfCHTL$_{584}$, which ran at about 90 kDa on the electrophoresis gel, was precipitated by adjusting the ammonium sulfate concentration from about 30% saturation to about 90% saturation. The PCfCHTL$_{584}$ was loaded, in three aliquots, onto a 5.0 ml, Metal chelating HiTrap™ column charged with NiCl$_2$, available from Amersham Pharmacia Biotech Inc., previously equilibrated with Nickel A buffer. The column was washed with Nickel A buffer until all unbound protein was removed. Bound PCfCHTL$_{584}$ was eluted with a linear gradient from 10 mM to 1 M imidazole in Nickel A buffer. The resulting column fractions were supplemented with Complete protease inhibitor cocktail, available from Roche Molecular Biochemicals, and analyzed for the presence of PCfCHTL$_{584}$ by immunoblot using an anti-PCfCHT$_{489}$ polyclonal antiserum. The results indicated that PCfCHTL$_{584}$ was eluted at about 100 mM imidazole.

The fractions containing PCfCHTL$_{584}$ were pooled and diafiltered into about 5 ml of Anion A buffer using a Centricon Plus 20 10-kDa concentrator. The PCfCHTL$_{584}$ protein was loaded onto a BioScale Q2 anion exchange column, available from Bio-Rad, Hercules, Calif., previously equilibrated with Anion A buffer. The column was washed with Anion A buffer until all unbound protein was removed. Protein bound to the column was eluted with a linear gradient from 10 mM to 1 M NaCl in Anion A buffer. The resulting fractions were analyzed for the presence of PCfCHTL$_{584}$ by coomassie-stained SDS-PAGE and immunoblot using anti-PCfCHT$_{489}$ polyclonal antiserum. The results indicated that PCfCHTL$_{584}$ was eluted at about 200 mM NaCl, and was about 50% pure.

EXAMPLE 2

The following example demonstrates the presence of chitinase enzymatic activity, indicating the presence of chitinase during several flea life stages.

Extracts of the following flea life stages were prepared, as follows: Tissue samples were isolated from unfed or bovine blood-fed *C. felis* first instar larvae, bovine blood-fed *C. felis* third instar larvae, bovine blood-fed *C. felis* wandering larvae, bovine blood-fed *C. felis* pupae, unfed or cat blood-fed adult *C. felis* midgut tissue, and unfed or cat blood-fed whole adult *C. felis* fleas. The midgut tissues were homogenized in Tris buffered saline (TBS, see Sambrook, ibid) by the standard freeze-fracture method and subsequent bath sonication, using a Branson 200 Ultrasonic cleaner, (available from VWR Scientific, Salt Lake City, Utah) for 30 seconds. Larval and pupal fleas were probe-sonicated at a setting of 4 for 20 seconds on a model W-380 sonicator (available from Heat Systems-Ultrasonics, Inc. Farmingdale, N.Y.). Whole adult fleas were ground with a microtube mortar and pestle and probe sonicated as above for 20 seconds. The extracts in all cases were centrifuged at about 16,000×g for about 20 minutes and the soluble material in the supernatants collected. Volumes of supernatant were adjusted with TBS such that 1 µl (microliter) of supernatant contained one flea or flea tissue equivalent.

Chitinase activity assays were performed on the above extracts as described below. The commercially available chitinase assay (available from Sigma, St. Louis, Mo.) used to detect flea chitinase activity is a two step enzymatic assay wherein chitinase hydrolyzes chitin (poly-β-(1,4)-N-acetyl-D-glucosamine) into chitobiose, which in turn is hydrolyzed by β-N-acetylglucosaminidase (NAGase) into N-acetyl-D-glucosamine. N-acetyl-D-glucosamine is then reacted with potassium tartrate and dinitrosalicylic acid to form a colored reaction product. One chitinase unit is defined as the amount of chitinase that will liberate 1.0 mg of N-acetyl-D-glucosamine from chitin per hour at pH 6 and 25° C. (in a two step reaction with NAGase from *Aspergillus niger*, available from Sigma.) The reaction substrate chitin was prepared by mixing shrimp chitin (available from Sigma) in 200 mM (milliMolar) KH$_2$PO$_4$, pH 6, 2 mM CaCl$_2$, such that the solution was 1.25% weight/volume shrimp chitin. The color reagent was prepared as follows: solution A was made by dissolving 12 g (gram) of potassium tartrate (available from Sigma) into 8 ml (milliliter) of a 2 M solution of sodium hydroxide, and then solution B was made by dissolving 0.485 g of 3,5-dinitrosalicylic acid (available from Sigma) into 20 ml of deionized water. Both solutions were heated to facilitate dissolution. To make the color reagent solution, solutions A and B were mixed and the volume brought to 40 ml with deionized water.

The reactions were initiated by mixing 200 µl (microliter) of chitin solution with about 25 flea equivalents, prepared as described above, and the reactions were carried out for two hours at 25° C. with constant mixing. The reactions were terminated by heating the reaction mixture in a boiling water bath for 5 minutes and then cooled. The second enzymatic step was initiated by adding 0.1 unit NAGase from *A. niger* (available from Sigma) to the cooled reaction mixtures. The reactions were allowed to proceed for 30 minutes at 25° C. The samples were briefly centrifuged in a mini-centrifuge to pellet chitin. 100 µl of supernatant was added to 150 µl of color reagent solution, volume was adjusted to 450 µl with deionized water, and the mixture was then heated to 100° C. for 5 minutes. The amount of N-acetyl-D-glucosamine was determined by reading absorbance of each assay at 540 nanometers, and comparing to a standard curve generated by commercially available N-acetyl-D-glucosamine (available from Sigma). The results are shown in Table 1.

TABLE 1

Chitinase activity in various flea extracts

| Flea extract, life stage | Chitinase (unit per flea equivalent) × 10$^{-3}$ |
| --- | --- |
| First instar, unfed | 0.425 |
| First instar, fed | 0.337 |
| Third instar | 2.462 |
| Wandering larvae | 1.145 |
| prepupae | 0.929 |
| pupae | 1.660 |
| unfed adult gut tissue | 0.381 |
| fed adult gut tissue | 0.425 |
| unfed adult fleas, whole | 0.359 |
| fed adult fleas, whole | 0.375 |

Chitinase activity was found to be highest in the flea third instar stage, second highest in the pupal stage, and third highest in the wandering and pre-pupal stages. There was no detectable chitinase activity in the unfed first instar fleas, fed first instar fleas, unfed adult fleas, fed adult fleas, unfed flea gut tissues, or fed flea gut tissues.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of: (a) a nucleic acid molecule comprising a nucleic acid sequence selected from the group consisting of SEQ ID NO:1, SEQ ID NO:3 SEQ ID NO:4, SEQ ID NO:6, SEQ ID NO:13, and SEQ ID NO:15; and (b) a nucleic acid molecule consisting of at least 18 consecutive nucleotides of a sequence as set forth in (a).

2. The nucleic acid molecule of claim 1, wherein said nucleic acid molecule is selected from the group consisting of SEQ ID NO:1, SEQ ID NO:3, SEQ ID NO:4, SEQ ID NO:6, SEQ ID NO:13, SEQ ID NO:15, SEQ ID NO:31, and SEQ ID NO:33.

3. An isolated nucleic acid molecule selected from the group consisting of: (a) a nucleic acid molecule that encodes a protein comprising an amino acid sequence selected from the group consisting of SEQ ID NO:2, SEQ ID NO:5 and SEQ ID NO:14; and (b) a nucleic acid molecule that encodes a protein consisting of at least 30 consecutive amino acids of a sequence as set forth in (a).

4. The nucleic acid molecule of claim 1, wherein said nucleic acid molecule encodes a protein comprising an amino acid sequence selected from the group consisting of SEQ ID:2, SEQ ID NO:5 SEQ ID NO:14 and SEQ ID NO:32.

5. A recombinant molecule comprising a nucleic acid molecule as set forth in claim 1 operatively linked to a transcription control sequence.

6. A recombinant cell comprising a nucleic acid molecule as set forth in claim 1.

7. A recombinant virus comprising a nucleic acid molecule as set forth in claim 1.

8. A method to produce a flea chitinase protein, said method comprising culturing a cell transformed with a nucleic acid molecule encoding said flea chitinase protein, wherein said nucleic acid molecule encodes an isolated protein selected from the group consisting of: (a) a protein comprising an amino acid sequence selected from the group consisting of SEQ ID NO:2, SEQ ID NO:5 and SEQ ID NO:14; and (b) a protein consisting of at least 30 consecutive amino acids of a sequence as set forth in (a).

9. A method to produce a flea chitinase protein, said method comprising culturing a cell transformed with a nucleic acid molecule encoding said flea chitinase protein, wherein said protein is encoded by an isolated nucleic acid molecule selected from the group consisting of: (a) a nucleic acid molecule comprising a nucleic acid sequence selected from the group consisting of SEQ ID NO:1, SEQ ID NO:4 and SEQ ID NO:13; and (b) a nucleic acid molecule consisting of at least 18 consecutive nucleotides of a sequence as set forth in (a).

10. A recombinant molecule comprising a nucleic acid molecule as set forth in claim 3 operatively linked to a transcription control sequence.

11. A recombinant cell comprising a nucleic acid molecule as set forth in claim 3.

12. A recombinant virus comprising a nucleic acid molecule as set forth in claim 3.

* * * * *